US007491865B2

(12) United States Patent
Vasioukhin et al.

(10) Patent No.: US 7,491,865 B2
(45) Date of Patent: Feb. 17, 2009

(54) MOUSE MODELS OF PROSTATE CANCER DEVELOPMENT AND METASTASIS THROUGH EXPRESSION OF A HEPSIN TRANSGENE

(75) Inventors: Valeri Vasioukhin, Seattle, WA (US); Robert J. Matusik, Brentwood, TN (US); Olga Klezovitch, Seattle, WA (US); John Chevillet, Seattle, WA (US)

(73) Assignees: Fred Hutchinson Cancer Research Center, Seattle, WA (US); Vanderbilt University, Nashville, TN (US)

( * ) Notice: Subject to any disclaimer, the term of this patent is extended or adjusted under 35 U.S.C. 154(b) by 121 days.

(21) Appl. No.: 11/208,257

(22) Filed: Aug. 19, 2005

(65) Prior Publication Data

US 2006/0101531 A1 May 11, 2006

Related U.S. Application Data

(60) Provisional application No. 60/603,043, filed on Aug. 19, 2004.

(51) Int. Cl.
G01N 33/00 (2006.01)
A01K 67/027 (2006.01)
C12N 15/00 (2006.01)

(52) U.S. Cl. .............................. 800/3; 800/10; 800/18; 800/22; 800/25

(58) Field of Classification Search .................. 800/3, 800/10, 13–18, 25
See application file for complete search history.

(56) References Cited

U.S. PATENT DOCUMENTS

| 2003/0049645 A1 | 3/2003 | Mu et al. |
| 2003/0175736 A1 | 9/2003 | Chinnaiyan et al. |
| 2004/0048255 A1 | 3/2004 | Chan et al. |
| 2004/0132156 A1 | 7/2004 | Parry et al. |

OTHER PUBLICATIONS

Cameron, E.R. Recent Advances in Transgenic Techology, Molec. Biotech. 1997, vol. 7, pp. 253-265.*
Sigmund, C.D. Viewpoint: Are Studies in Genetically Altered Mice Out of Control. Arteroscler. Throm. Vasc. Biol. 2000, vol. 20, pp. 1425-1429.*
Niemann, H. Transgenic Farm Animals Get Off the Ground. Transg. Res. 1998, vol. 7, pp. 73-75.*
Smith. Gene Transfer in Higher Animals: Theoretical Considerations and Key Concepts. J. Biotech. 2002, vol. 99, pp. 1-22.*
Montoliu. Gene Transfer Strategies in Animal Transgenesis. Cloning and Stem Cells. 2002, vol. 4, pp. 39-46.*
Ristevski. Making Better Transgenic Models. Molecular Biotechnology, vol. 29, pp. 153-163.*
Yeung et al. Predisposition to Renal Carcinoma in the Eker Rat is Determined by Germ-Line Mutation of the Tuberous Sclerosis 2 (TSC2) Gene. Proced. Natl. Acad. Sci. Nov. 1994, vol. 91, pp. 11413-11416.*
Wu. Gene Targeting in Hemostasis. Hepsin. Frontiers in Bioscience. Feb. 1, 2001, vol. 6, pp. 1-17.*
Su et al. Consequences of Expression of Hepsin in Murine Vascular Systems. Journal of Thrombosis and Haemostasis. 2003, vol. 1., Suppl. 1, abstract P1730, meeting Jul. 12-18, 2003.*
Kawamura et al. Complete Nucleotide Sequence, Origin of Isoform and Functional Characterization of the Mouse Hepsin Gene. European J. Biochem. 1999, vol. 262, pp. 755-764.*
Masumori et al. A Probasin-Large T Antigen Transgenic Mouse Line Develops Prostate Adenocarcinoma and Neuroendocrine Carcinoma with Metastatic Potential. Cancer Res., Mar. 1, 2001, vol. 61, pp. 2239-2249.*
Kananen et al. Gonadal Tumorigenesis in Transgenic Mice Bearing the Mouse Inhibin Alpha-Subunit Promoter/Simian Virus T-Antigen Fusion Gene: Characterization of Ovarian Tumors and Establishment of Gonadotropin-Responsive Granulosa Cell Lines. Molecular Endocrinology. 1995, vol. 9, pp. 616-627.*
Abate-Shen and Shen, "Molecular genetics of prostate cancer," *Genes Dev.*, 14:2410-2434 (2000).
Bernards and Weinberg, "A progression puzzle," *Nature*, 418:823 (2002).
Chen et al., "Hepsin and maspin are inversely expressed in laser capture microdissected prostate cancer," *J. Urol.*, 169:1316-1319 (2003).
Del Rosso et al., "Multiple pathways of cell invasion are regulated by multiple families of serine proteases," *Clin. Exp. Metastasis*, 19:193-207 (2002).
Dhanasekaran et al., "Delineation of prognostic biomarkers in prostate cancer," *Nature*, 412:822-826 (2001).
Ernst et al., "Decrease and gain of gene expression are equally discriminatory markers for prostate carcinoma: a gene expression analysis on total and microdissected prostate tissue," *Am. J. Pathol.*, 160:2169-2180 (2002).
Ihara et al., "Prometastatic effect of N-acetylglucosaminyltransferase V is due to modification and stabilization of active matriptase by adding β1-6 GlcNAc branching," *J. Biol. Chem.*, 277:16960-16967 (2002).
Kasper et al., "Development, progression and androgen-dependence of prostate tumors in probasin-large T antigen transgenic mice: a model for prostate cancer," *Lab. Invest.*, 78:319-333 (1998).
Kazama et al., "Hepsin, a putative membrane-associated serine protease, activates human factor VII and initiates a pathway of blood coagulation on the cell surface leading to thrombin formation," *J. Biol. Chem.*, J. Biol. Chem., 270:66-72 (1995).
Klezovitch, et al., "Hepsin promotes prostate cancer progression and metastasis," *Cancer Cell*, 6:185-195 (2004).
Lin et al., "Prostate-localized and androgen-regulated expression of the membrane-bound serine protease TMPRSS2," *Cancer Res.*, 59:4180-4184 (1999).
Luo et al., "Human prostate cancer and benign prostatic hyperplasia: Molecular dissection by gene expression profiling," *Cancer Res.*, 61:4683-4688 (2001).
Magee et al., "Expression profiling reveals hepsin overexpression in prostate cancer," *Cancer Res.*, 61:5692-5696 (2001).

(Continued)

*Primary Examiner*—Deborah Crouch
(74) *Attorney, Agent, or Firm*—Townsend and Townsend and Crew LLP

(57) ABSTRACT

Transgenic, non-human animal model of cancer, methods of making such animals and methods of using such animals to screen test compounds are provided.

19 Claims, 8 Drawing Sheets
(2 of 8 Drawing Sheet(s) Filed in Color)

OTHER PUBLICATIONS

Netzel-Arnett et al., "Membrane anchored serine proteases: a rapidly expanding group of cell surface proteolytic enzymes with potential roles in cancer," *Cancer Metastasis Rev.*, 22:237-258 (2003).

Orsulic, "An RCAS-TVA-based approach to designer mouse models," *Mamm. Genome.*, 13:543-547 (2002).

Robinson et al., "The basic biology of metastasis," *Cancer Treat Res.*, 118:1-21 (2004).

Srikantan et al., "*Hepsin* inhibits cell growth/invasion in prostate cancer cells," *Cancer Res.*, 62:6812-6816 (2002).

Stamey et al., "Molecular genetic profiling of Gleason grade 4/5 prostate cancers compared to benign prostatic hyperplasia," *J. Urol.*, 166:2171-2177 (2001).

Stephan et al., "Hepsin is highly over expressed in and a new candidate for a prognostic indicator in prostate cancer," *J. Urol.*, 171:187-191 (2004).

Takeuchi et al., "Cellular localization of membrane-type serine protease 1 and identification of protease-activated receptor-2 and single-chain urokinase-type plasminogen activator as substrates," *J. Biol. Chem.*, 275:26333-26342 (2000).

Takeuchi et al., "Reverse biochemistry: Use of macromolecular protease inhibitors to dissect complex biological processes and identify a membrane-type serine protease in epithelial cancer and normal tissue," *Proc. Natl. Acad. Sci. USA*, 96:11054-11061 (1999).

Tanimoto et al., "Hepsin, a cell surface serine protease identified in hepatoma cells, is overexpressed in ovarian cancer," *Cancer Res.*, 57:2884-2887 (1997).

Wallrapp et al., "A novel transmembrane serine protease (TMPRSS3) overexpressed in pancreatic cancer," *Cancer Res.*, 60:2602-2606 (2000).

Welsh et al., "Analysis of gene expression identifies candidate markers and pharmacological targets in prostate cancer," *Cancer Res.*, 61:5974-5978 (2001).

Wu, "Type II transmembrane serine proteases," *Curr. Top Dev. Biol.*, 54:167-206 (2003).

Yan et al., "Corin, a mosaic transmembrane serine protease encoded by a novel cDNA from human heart," *J. Biol. Chem.*, 274:14926-14935 (1999).

Zhang et al., "A small composite probasin promoter confers high levels of prostate-specific gene expression through regulation by androgens and glucocorticoids in vitro and in vivo," *Endocrinology*, 141:4698-4710 (2000).

\* cited by examiner

Figure 8.

```
              9          18          27          36          45          54          63          72
GAC AUG GCG AAG GAG GGU GGC CGG ACU GCA GCA UGC UGC UCC AGA CCC AAG GUG GCA GCU CUC AUU GUG GGU
    Met Ala Lys Glu Gly Gly Arg Thr Ala Ala Cys Cys Ser Arg Pro Lys Val Ala Ala Leu Ile Val Gly>

81          90          99         108         117         126         135         144
ACC CUG CUG UUC CUG ACA GGC AUU GGG GCC GCG UCC UGG GCC AUU GUG ACC AUC CUA CUG CAG AGU GAC CAG
Thr Leu Leu Phe Leu Thr Gly Ile Gly Ala Ala Ser Trp Ala Ile Val Thr Ile Leu Leu Gln Ser Asp Gln>

153         162         171         180         189         198         207         216
GAG CCA CUG UAC CAA GUG CAG CUC AGU CCA GGG GAC UCA CGA CUU GCA GUG UUG GAC AAG ACG GAG GGU ACG
Glu Pro Leu Tyr Gln Val Gln Leu Ser Pro Gly Asp Ser Arg Leu Ala Val Leu Asp Lys Thr Glu Gly Thr>

225         234         243         252         261         270         279         288
UGG AGG CUA CUG UGC UCC UCA CGC UCC AAU GCC AGG GUG GCA GGG CUC GGC UGU GAG GAG AUG GGC UUU CUC
Trp Arg Leu Leu Cys Ser Ser Arg Ser Asn Ala Arg Val Ala Gly Leu Gly Cys Glu Glu Met Gly Phe Leu>

297         306         315         324         333         342         351         360
AGG GCU CUG GCG CAC UCG GAG CUG GAU GUG CGC ACU GCG GGC GCC AAC GGC ACA UCG GGC UUC UUU UGC GUG
Arg Ala Leu Ala His Ser Glu Leu Asp Val Arg Thr Ala Gly Ala Asn Gly Thr Ser Gly Phe Phe Cys Val>

369         378         387         396         405         414         423         432
GAC GAG GGC GGA CUG CCU CUG GCU CAG AGG UUG CUG GAU GUC AUC UCU GUA UGU GAC UGU CCU AGA GGC CGA
Asp Glu Gly Gly Leu Pro Leu Ala Gln Arg Leu Leu Asp Val Ile Ser Val Cys Asp Cys Pro Arg Gly Arg>

441         450         459         468         477         486         495         504
UUC CUG ACU GCC ACC UGC CAA GAC UGU GGC CGC AGG AAG CUG CCG GUG GAC CGC AUU GUG GGG GGC CAG GAC
Phe Leu Thr Ala Thr Cys Gln Asp Cys Gly Arg Arg Lys Leu Pro Val Asp Arg Ile Val Gly Gly Gln Asp>

513         522         531         540         549         558         567         576
AGC AGU CUG GGA AGG UGG CCG UGG CAG GUC AGC CUG CGU UAU GAU GGG ACC CAC CUC UGU GGG GGG UCC CUG
Ser Ser Leu Gly Arg Trp Pro Trp Gln Val Ser Leu Arg Tyr Asp Gly Thr His Leu Cys Gly Gly Ser Leu>

585         594         603         612         621         630         639         648
CUG UCU GGG GAC UGG GUG CUG ACU GCU GCA CAU UGC UUU CCA GAG CGG AAC CGG GUC CUG UCU CGG UGG CGA
Leu Ser Gly Asp Trp Val Leu Thr Ala Ala His Cys Phe Pro Glu Arg Asn Arg Val Leu Ser Arg Trp Arg>

657         666         675         684         693         702         711         720
GUA UUU GCU GGU GCU GUA GCC CGG ACC UCA CCC CAU GCU GUG CAA CUG GGG GUU CAG GCU GUG AUC UAU CAU
Val Phe Ala Gly Ala Val Ala Arg Thr Ser Pro His Ala Val Gln Leu Gly Val Gln Ala Val Ile Tyr His>

729         738         747         756         765         774         783         792
GGG GGC UAC CUU CCC UUU CGA GAC CCU ACU AUU GAC GAA AAC AGC AAU GAC AUU GCC UUG GUC CAC CUC UCU
Gly Gly Tyr Leu Pro Phe Arg Asp Pro Thr Ile Asp Glu Asn Ser Asn Asp Ile Ala Leu Val His Leu Ser>

801         810         819         828         837         846         855         864
AGC UCC CUG CCU CUC ACA GAA UAC AUC CAG CCA GUG UGU CUC CCU GCU GCG GGA CAG GCC CUG GUG GAU GGC
Ser Ser Leu Pro Leu Thr Glu Tyr Ile Gln Pro Val Cys Leu Pro Ala Ala Gly Gln Ala Leu Val Asp Gly>

873         882         891         900         909         918         927         936
AAG GUC UGU ACU GUG ACC GGC UGG GGU AAC ACA CAG UUC UAU GGC CAA CAG GCU AUG GUG CUC CAA GAG GCC
Lys Val Cys Thr Val Thr Gly Trp Gly Asn Thr Gln Phe Tyr Gly Gln Gln Ala Met Val Leu Gln Glu Ala>

945         954         963         972         981         990         999        1008
CGG GUU CCC AUC AUA AGC AAC GAA GUU UGC AAC AGC CCC GAC UUC UAC GGG AAU CAG AUC AAG CCC AAG AUG
Arg Val Pro Ile Ile Ser Asn Glu Val Cys Asn Ser Pro Asp Phe Tyr Gly Asn Gln Ile Lys Pro Lys Met>

1017        1026        1035        1044        1053        1062        1071        1080
UUC UGU GCU GGC UAU CCU GAG GGU GGC AUU GAU GCG UGC CAG GGC GAC AGU GGA GGC CCC UUU GUG UGU GAA
Phe Cys Ala Gly Tyr Pro Glu Gly Gly Ile Asp Ala Cys Gln Gly Asp Ser Gly Gly Pro Phe Val Cys Glu>

1089        1098        1107        1116        1125        1134        1143        1152
GAC AGC AUC UCU GGG ACA UCA AGG UGG CGG CUA UGU GGC AUU GUA AGC UGG GGU ACC GGC UGU GCU UUG GCC
Asp Ser Ile Ser Gly Thr Ser Arg Trp Arg Leu Cys Gly Ile Val Ser Trp Gly Thr Gly Cys Ala Leu Ala>

1161        1170        1179        1188        1197        1206        1215        1224
CGG AAG CCA GGA GUG UAC ACC AAA GUC ACU GAC UUC CGG GAG UGG AUC UUC AAG GCC AUA AAG ACU CAC UCC
Arg Lys Pro Gly Val Tyr Thr Lys Val Thr Asp Phe Arg Glu Trp Ile Phe Lys Ala Ile Lys Thr His Ser>

1233        1242        1251        1260        1269        1278        1287        1296
GAA GCC AGU GGC AUG GUG ACU CAG CCC UGA UCC CGC CUC AUC UCG CUG CUC CGU GCU GCA CUA GCA UCC AGA
Glu Ala Ser Gly Met Val Thr Gln Pro Xxx>
```

MOUSE MODELS OF PROSTATE CANCER DEVELOPMENT AND METASTASIS THROUGH EXPRESSION OF A HEPSIN TRANSGENE

CONTINUITY

This application claims the benefit of U.S. Provisional Application No. 60/603,043 filed Aug. 19, 2004, which is incorporated by reference herein in its entirety.

STATEMENT AS TO RIGHTS TO INVENTIONS MADE UNDER FEDERALLY SPONSORED RESEARCH AND DEVELOPMENT

The present invention was developed in part with government support under grant numbers R01 CA102365, R01-CA76142 and U01 CA84239 awarded by the National Cancer Institutes. The government my have +–certain rights in this invention.

BACKGROUND OF THE INVENTION

The majority of cancer-related deaths are associated with metastasis. The metastatic cascade is a complex process consisting of a number of important steps that include loss of tissue architecture, local invasion, invasion into blood and lymph vessels, extravasation, establishment of the secondary foci and angiogenesis. Very little is known about the mechanisms of metastasis. While it is clear the metastatic process is driven by genetic modifications in tumor cells, the identity of involved genes and their function remain unknown. The lack of mechanistic knowledge about metastasis represents a significant block on the road of development new and efficient therapies to treat cancer patients.

Animal models of human cancer are an important part of research directed toward finding a cure for cancer. Cancer development and especially formation of metastases at the distant organs is a complex process that is difficult to replicate using cells growing outside of the body (e.g., in an incubator). Genetically engineered mice have been used to model cancer development; however, a significant limitation of existing mouse models is an extremely low rate of metastasis formation, especially metastases to the bone. As a result, the metastatic process can not be replicated to study its mechanisms. In addition, the low frequency of metastasis in mouse models makes it difficult to test the efficacy of potential drugs for treatment of human patients with metastatic cancer.

Hepsin is a type-II transmembrane serine protease that is markedly upregulated in human prostate and ovarian cancer. For example, DNA microarray studies of gene expression in human prostate carcinomas have revealed marked overexpression of hepsin mRNA (Chen et al., *J. Urol.* 169:1316-1319 (2003); Dhanasekaran et al., *Nature* 412:822-826 (2001); Ernst et al., *Am. J. Pathol.* 160:2169-2180 (2002); Luo et al., *Cancer Res.* 61:4683-4688 (2001); Magee et al., *Cancer Res.* 61:5692-5696 (2001); Stamey et al., *J. Urol.* 166:2171-2177 (2001); Stephan et al., *J. Urol.* 171:187-191 (2004); Welsh et al., *Cancer Res.* 61:5974-5978 (2001)). Hepsin mRNA is upregulated in 90% of prostate tumors, with levels often increased greater than 10 fold, and exclusively expressed in tumor cells. Upregulation of hepsin RNA levels was reported to be accompanied by an increase in protein levels (Dhanasekaran et al., 2001). The significance of this upregulation and overall role of hepsin in cancer progression and metastasis is unknown, however. For example, it is not clear how hepsin mRNA levels correlate with different stages/grades of prostate cancer. Although initial studies showed that hepsin levels were highest in prostatic intraepithelial neoplasia (PIN) and decrease with prostate cancer progression (Dhanasekaran et al., 2001), other studies have demonstrated that hepsin mRNA levels increase with prostate cancer progression and reach maximum levels in more advanced (Gleason grade 4/5) prostate carcinomas (Chen et al., 2003; Stamey et al., 2001). At present, it is unclear if overexpression of hepsin in prostate cancer cells plays a role in prostate cancer development or progression.

BRIEF SUMMARY OF THE INVENTION

The present invention provides transgenic, non-human animals expressing a hepsin transgene. In some embodiments, the transgenic, non-human animal has a genetic predisposition to develop a cancerous or precancerous condition in a tissue or organ of the animal. The hepsin transgene is expressed in the tissue or organ of interest. For example, the hepsin transgene can be expressed in the prostate or ovaries. In some embodiments, the hepsin transgene is overexpressed, as compared with the endogenous hepsin gene.

The hepsin transgene can be, for example, a mouse transgene or a cognate, heterologous hepsin transgene, such as, for example, a human transgene. In some embodiments, the hepsin transgene is operably linked to a tissue specific promoter. For example, the tissue specific promoter can be a probasin promoter for expression in prostate epithelial cells or an inhibit-alpha gene promoter/enhancer for expression in ovarian cells.

In some embodiments, the animal is a prostate cancer model or an ovarian cancer model. For example, the animal prostate cancer model can be a LPB-Tag mouse. The transgenic animal can be, for example, a rodent, such as a mouse or a rat.

In some embodiments, primary prostate cancer progression or metastasis is increased in the transgenic animal, as compared with a control animal having the same genetic predisposition, but not expressing the hepsin transgene. In some embodiments, the transgenic animal has increased metastasis of the cancer to the liver, lung and/or bone.

In another aspect, a method of producing a transgenic mammal suitable for screening agents for use in the prophylaxis or treatment of cancer is provided. The method includes forming a transgenic mammal comprising a diploid genome encoding a hepsin transgene; selecting one of the transgenic mammals wherein the hepsin transgene is expressed to produce a hepsin polypeptide, and wherein the hepsin polypeptide exhibits tissue-specific expression. The transgenic animal can be breed to an animal of the same species that has a genetic predisposition for the cancer to form a progeny transgenic animal(s). A progeny transgenic animal expressing the hepsin transgene and having the predisposition for the cancer can be selected. The transgenic animal can be, for example, a mammal such as a mouse or rat. The genetic predisposition for cancer can be, for example, a genetic predisposition for prostate cancer or ovarian cancer. The hepsin transgene can be, for example, a mouse transgene or a cognate, heterologous transgene, such as, for example, a human hepsin transgene.

In another aspect, a method of screening an agent for use in prophylaxis or treatment of cancer is provided. The method includes providing a transgenic animal, such as a mammal, comprising a diploid genome, having a genetic predisposition for cancer or a precancerous condition and encoding a hepsin transgene, wherein the hepsin transgene is expressed. The transgenic animal can be contacted with the test compound at a dosage of suitable dosage. For example, the dosage can be within the range of about 1 ng/kg to about 10 mg/kg. The contacted transgenic animal is examined to determine whether the test compound affects tumor development, progression and/or metastasis. In some embodiments, the dosage of the test compound is from about 10 µg/kg to about 1 mg/kg. In some embodiments, the candidate substance does not inhibit hepsin.

The animal can be, for example, a mammal such as a rodent (e.g., a mouse or rat). The genetic predisposition for cancer can be, for example, a genetic predisposition for prostate (e.g., an LPB-Tag mouse) or ovarian cancer. In some embodiments, the test substance decreases metastasis to the liver, lung and/or bone.

For a fuller understanding of the various embodiments of the invention, reference is made to the following description taken in connection with the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

PB-hepsin animals are positive for PB-hepsin transgene (Hepsin-IRES-GFP), T-antigen (Tag), synaptophysin (Syn), and androgen receptor (AR) expression. PB-hepsin transgene expression was determined by in situ hybridization (I). Expression of T-antigen, synaptophysin and androgen receptor was revealed by immunohistochemistry (J-L). The scale bar in L corresponds to 0.5 mm in C, E, G, 0.3 mm in J-L, 150 μm in I and 50 μm in D, F, H.

Figure 7:
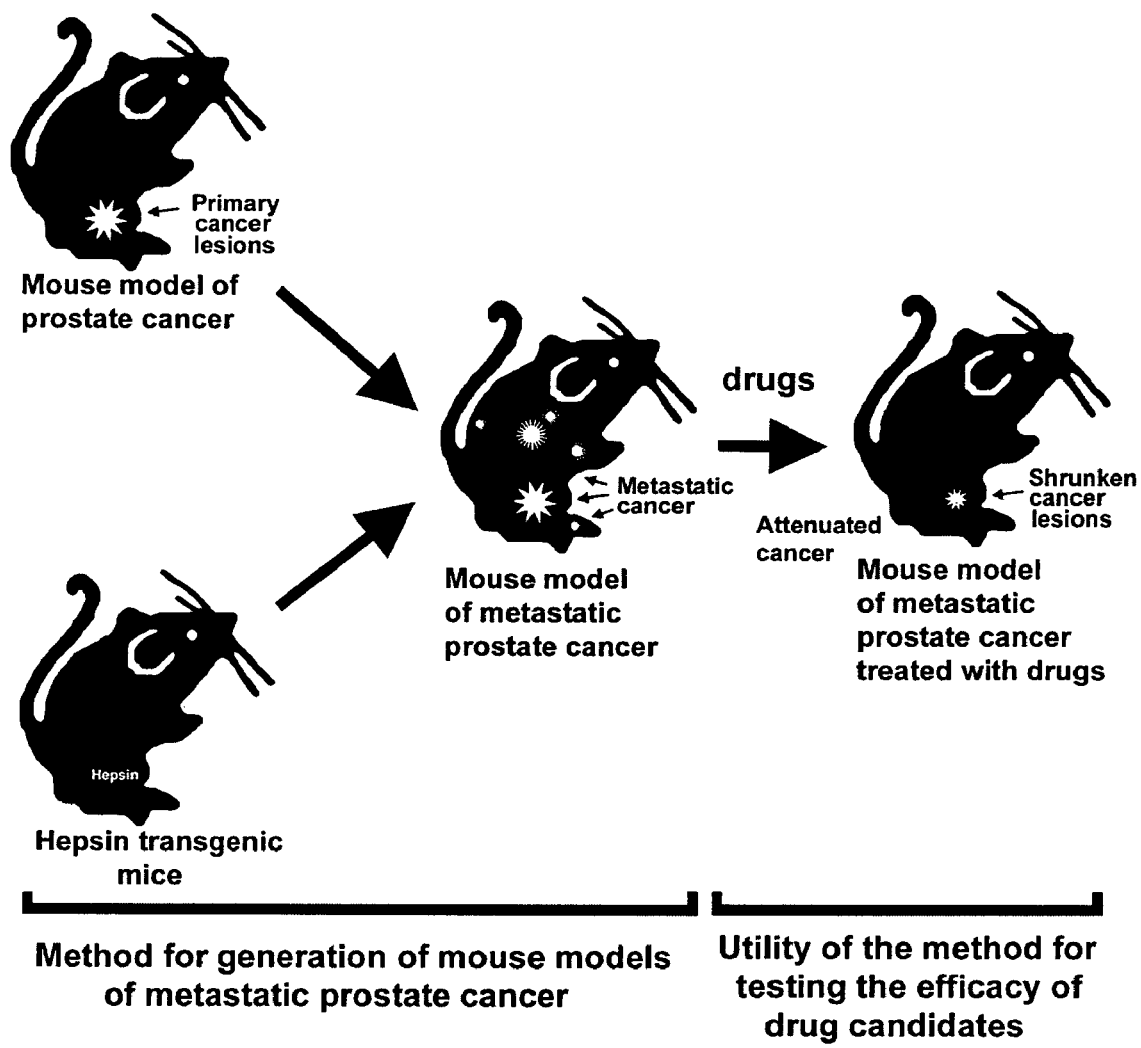

FIG. 7. A diagram demonstrating a method of making a mouse model of prostate cancer.

FIG. 8. Nucleotide sequence encoding (SEQ ID NO:7), and the protein sequence of (SEQ ID NO:8), mouse hepsin.

DETAILED DESCRIPTION OF THE INVENTION

The present inventors have discovered that hepsin plays a causative role in cancer progression and metastasis formation. An increase in hepsin levels leads to the development of more advanced primary tumors in the original tissue or organ and/or subsequent frequent and prominent formation of secondary metastatic lesions in the distant organs, such as the bone.

In one aspect, a transgenic, non-human animal model of cancer is provided. The transgenic animal can express or overexpress a hepsin transgene. The animal model exhibits more advanced primary tumors in the original tissue or organ, and/or more frequent metastasis formation, as compared with an animal model not overexpressing hepsin.

In another aspect, a method is provided to increase progression to cancer development and/or metastasis in an animal cancer model by introducing a hepsin transgene into the animal model. Expression of the hepsin transgene leads to the development of more advanced primary tumors and/or more frequent metastasis formation, as compared with an animal model not expressing the hepsin transgene.

The transgenic animal model also provides a tool for studying cancer progression, metastases formation and/or for the identification and testing of test compounds (e.g., drug candidates) for the prophylaxis and/or treatment of cancer and other hyperplasia. For example, a transgenic animal model may develop rapid and frequent metastasis to multiple organs, including bone, as compared with a transgenic animal model not expressing the hepsin transgene.

Hepsin protein is a type-II transmembrane serine protease. The hepsin protein can be a "homologous" or "heterologous polypeptide." A "heterologous polypeptide," also referred to as a "xenogenic polypeptide," is a polypeptide having an amino acid sequence found in an organism not consisting of the transgenic nonhuman animal. As used herein, the term "polypeptide" refers to a polymer of amino acids and its equivalent and does not refer to a specific length of the product; thus, peptides, oligopeptides and proteins are included within the definition of a polypeptide. A derivative is a polypeptide having conservative amino acid substitutions, as compared with another sequence. Derivatives further include other modifications of proteins, including, for example, modifications such as glycosylations, acetylations, phosphorylations, and the like.

The hepsin protein can be, for example, a human or non-human mammalian protein. Suitable hepsin proteins are, for example, hepsin proteins encoded by human Unigene Cluster Hs.432750, mouse Unigene Cluster Mm.19182, mouse IMAGE clone #747832, rat Unigene Cluster Rn.11139, or the like. The hepsin protein also can be a modified hepsin, such as, for example, those disclosed in U.S. Patent Publication Nos. 2004/0048255 and 2004/0132156 (the disclosures of which are incorporated by reference herein).

The hepsin protein is typically encoded by a hepsin transgene. A "hepsin transgene" refers to a nucleic acid encoding a hepsin protein or a functionally active fragment thereof. The hepsin transgene can be, for example, a portion of genomic DNA, cDNA, mRNA, RNA or a fragment thereof encoding a functional hepsin protein (e.g., a full length hepsin protein) or a functionally active fragment of a hepsin protein. The term "functionally active" refers to a fragment, derivative or analog having one or more functions associated with a full-length (wild-type) hepsin polypeptide (e.g., hepsin enzyme activity).

The hepsin transgene can be from the same species as the transgenic animal (e.g., a mouse hepsin transgene overexpressed in a mouse). In some embodiments, the hepsin transgene is a cognate heterologous hepsin transgene. A cognate heterologous hepsin transgene refers to a corresponding gene from another species; thus, if murine hepsin is the reference, human hepsin is a cognate heterologous gene (as is porcine, ovine, or rat hepsin, along with hepsin genes from other species). In some embodiments, the hepsin transgene can encode a human hepsin protein or a functionally active fragment thereof. The human hepsin transgene can be, for example, from human Unigene Cluster Hs.432750. In other embodiments, the hepsin transgene encodes a non-human hepsin protein or a functionally active fragment thereof. The non-human hepsin can be, for example, a mouse, rat, hamster, gerbil, rabbit, bovine, dog, chicken, monkey or other mammalian hepsin. The non-human hepsin transgene can be, for example from mouse Unigene Cluster Mm.19182, mouse IMAGE clone #747832, rat Unigene Cluster Rn.11139, or the like.

A transgene containing various gene segments encoding a cognate heterologous protein sequence may be readily identified, e.g. by hybridization or DNA sequencing, as being from a species of organism other than the transgenic animal. In some embodiments, the cognate hepsin transgene is at least 75%, at least 80%, at least 85%, at least 90% or at least 95% identical to the homologous hepsin transgene. As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence, as measured using one of the following sequence comparison algorithms, or by visual inspection. The phrase "substantially identical," in the context of two nucleic acids or polypeptides, refers to two or more sequences or subsequences that have at least 60%, typically 80%, most typically 90-95% nucleotide or amino acid residue identity, when compared and aligned for maximum correspondence, as measured using one of the following sequence comparison algorithms, or by visual inspection. An indication that two polypeptide sequences are "substantially identical" is that one polypeptide is immunologically reactive with antibodies raised against the second polypeptide.

In some embodiments, the cognate hepsin protein is at least 75%, at least 80%, at least 85%, at least 90% or at least 95% similar to the homologous hepsin protein. As used herein, "similarity" or "percent similarity" in the context of two or polypeptide sequences, refer to two or more sequences or subsequences that are the same or have a specified percentage of amino acid residues or conservative substitutions thereof, that are the same, when compared and aligned for maximum correspondence, as measured using one of the following sequence comparison algorithms, or by visual inspection. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art, as discussed below.

The term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions.

The term "conservative substitution," when describing a polypeptide, refers to a change in the amino acid composition of the polypeptide that does not substantially alter the polypeptide's activity. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions."

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

A hepsin transgene also can be identified, for example, by expression of the hepsin transgene from an expression library. (See, e.g., Sambrook et al. (2001). *Molecular cloning: a laboratory manual*, 3rd ed. (Cold Spring Harbor, N.Y., Cold Spring Harbor Laboratory Press); Ausubel et al., supra.) A mutated endogenous gene sequence can be referred to as a heterologous transgene; for example, a transgene encoding a mutation in a murine hepsin gene which is not known in naturally-occurring murine genomes is a heterologous transgene with respect to murine and non-murine species. The hepsin transgene also can encode a modified hepsin, such as, for example, those disclosed in U.S. Patent Publication Nos. 2004/0048255 and 2004/0132156 (the disclosures of which are incorporated by reference herein).

In some embodiments, the hepsin transgene is expressed from an expression construct comprising a transcriptional unit. A "transcriptional unit" refers to a polynucleotide sequence that comprises a hepsin transgene (e.g., the structural gene (exons)) or a functionally active fragment thereof, a cis-acting linked promoter and other cis-acting sequences necessary for efficient transcription of the structural sequences, distal regulatory elements necessary for appropriate tissue-specific and developmental transcription of the structural sequences (as appropriate), and additional cis sequences for efficient transcription and translation (e.g., polyadenylation site, mRNA stability controlling sequences, or the like). Regulatory or other sequences useful in expression vectors can form part of the transgene sequence. This includes intronic sequences and polyadenylation signals, if not already included.

The promoter and other cis-acting sequences are operably linked to the structural gene. As used herein, the term "operably linked" refers to a linkage of polynucleotide (also referred to as a nucleic acid) elements in a functional relationship. A nucleic acid is "operably linked" when it is placed into a functional relationship with another nucleic acid sequence. For instance, a promoter or enhancer is operably linked to a coding sequence if it effects the transcription of the coding sequence. "Operably linked" means, for example, that the DNA sequences being linked are typically contiguous and, where necessary to join two protein coding regions, contiguous and in reading frame. As used herein, "linked" means in polynucleotide linkage (i.e., phosphodiester linkage). "Unlinked" means not linked to another polynucleotide sequence; hence, two sequences are unlinked if each sequence has a free 5' terminus and a free 3' terminus.

In some embodiments, the promoter is a tissue-specific promoter. For example, the following animal transcriptional control regions, which exhibit tissue specificity, have been utilized for transgenic expression animals: the elastase I gene control region which is active in pancreatic acinar cells (Swift et al., *Cell* 38:639-46 (1984); Ornitz et al., *Cold Spring Harbor Symp. Quant. Biol.* 50:399-409 (1986); MacDonald, *Hepatology* 7(1 Suppl.):42S-51S (1987); the insulin gene control region which is active in pancreatic beta cells (Hanahan, *Nature* 315:115-22 (1985)); the immunoglobulin gene control region which is active in lymphoid cells (Grosschedl et al., *Cell* 38:647-58 (1984); Adams et al., *Nature* 318:533-38 (1985); Alexander et al., *Mol. Cell. Biol.* 7:1436-44 (1987)); the mouse mammary tumor virus control region which is active in testicular, breast, lymphoid and mast cells (Leder et al., *Cell* 45:485-95 (1986)); the albumin gene control region which is active in liver (Pinkert et al., *Genes Dev.* 1:268-76 (1987)); the alpha-fetoprotein gene control region which is active in liver (Krumlauf et al., *Mol. Cell. Biol.* 5:1639-48 (1985); Hammer et al., *Science* 235:53-58 (1987)); the alpha 1-antitrypsin gene control region which is active in the liver (Kelsey et al., *Genes and Devel.* 1:161-71 (1987)); the beta-globin gene control region which is active in myeloid cells (Magram et al., *Nature* 315:338-40 (1985); Kollias et al., *Cell* 46:89-94 (1986)); the myelin basic protein gene control region which is active in oligodendrocyte cells in the brain (Readhead et al., *Cell* 48:703-12 (1987)); the myosin light chain-2 gene control region which is active in skeletal muscle (Shani, *Nature* 314:283-86 (1985)); and the gonadotropic releasing hormone gene control region which is active in the hypothalamus (Mason et al., *Science* 234:1372-78 (1986)). In an exemplary embodiment, the promoter is the probasin promoter (Zhang et al., *Endocrinology* 141:4698-4710 (2000)) for expression in prostate epithelial cells.

A transgenic non-human animal can be produced which contains selected systems that allow for regulated expression of the hepsin transgene. One example of such a system is the cre/loxP recombinase system of bacteriophage P1. For a description of the cre/loxP recombinase system, see, e.g., Lakso et al. (*Proc. Natl. Acad. Sci. USA* 89:6232-36 (1992)). Another example of a recombinase system is the FLP recombinase system of *S. cerevisiae* (see, e.g., O'Gorman et al., *Science* 251:1351-55 (1991)). If a cre/loxP recombinase system is used to regulate expression of the transgene, animals containing transgenes encoding both the Cre recombinase and a selected protein is used. Such animals can be provided through the construction of "double" transgenic animals, e.g., by mating two transgenic animals, one containing a transgene encoding a selected protein and the other containing a transgene encoding a recombinase.

In some embodiments, the hepsin transgene is integrated into the genome of a cell of the transgenic animal. The cell can be a somatic cell or a germline cell. In some embodiments, the hepsin transgene is integrated into the genome of a cell from which a transgenic animal develops and which remains in the genome of the mature animal in one or more cell types or tissues of the transgenic animal.

Hepsin transgenes can be overexpressed in a non-human animal such as a mammal. The mammal can be, for example, a rodent such as a mouse, hamster, guinea pig, rabbit or rat, a primate, a porcine, an ovine, a bovine, a feline, a canine, and the like. In specific embodiments, the transgenic animal can be a sheep, goat, horse, cow, bull, pig, rabbit, guinea pig, hamster, rat, gerbil, mouse, or the like. In other embodiments, the animal can be a bird. In some embodiments, the animal is a chimeric animals (i.e., those composed of a mixture of genetically different cells), a mosaic animals (i.e., an animal composed of two or more cell lines of different genetic origin or chromosomal constitution, both cell lines derived from the same zygote), an immature animal, a fetus, a blastula, and the like.

Transgenic, non-human animals containing a hepsin transgene can be prepared by methods known in the art. In general, a hepsin transgene is introduced into target cells, which are then used to prepare a transgenic animal. A hepsin transgene can be introduced into target cells, such as for example, pluripotent or totipotent cells such as embryonic stem (ES) cells (e.g., murine embryonal stem cells) or other stem cells (e.g., adult stem cells); germ cells (e.g., primordial germ cells, oocytes, eggs, spermatocytes, or sperm cells); fertilized eggs; zygotes; blastomeres; fetal or adult somatic cells (either differentiated or undifferentiated); and the like. In some embodiments, a hepsin transgene is introduced into embryonic stem cells or germ cells of animals (e.g., a rodent) to prepare a transgenic animal overexpressing hepsin.

Methods for generating transgenic animals via embryo manipulation and microinjection, particularly animals such as mice, are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986).

Embryonic stem cells can be manipulated according to published procedures (see, e.g., *Teratocarcinomas and Embryonic Stem Cells: A Practical Approach*, Robertson (ed.), IRL Press, Washington, D.C. (1987); Zjilstra et al., *Nature* 342:435-38 (1989); Schwartzberg et al., *Science* 246: 799-803 (1989); U.S. Pat. Nos. 6,194,635; 6,107,543; and 5,994,619; each of which is incorporated herein by reference in their entirety). Methods for isolating primordial germ cells are well known in the art. For example, methods of isolating primordial germ cells from ungulates are disclosed in U.S. Pat. No. 6,194,635 (the disclosure of which is incorporated by reference herein in its entirety).

A hepsin transgene can be introduced into a target cell by any suitable method. For example, a hepsin transgene can be introduced into a cell by transfection (e.g., calcium phosphate or DEAE-dextran mediated transfection), lipofection, electroporation, microinjection (e.g., by direct injection of naked DNA), biolistics, infection with a viral vector containing a hepsin transgene, cell fusion, chromosome-mediated gene transfer, microcell-mediated gene transfer, nuclear transfer, and the like. A hepsin transgene can be introduced into cells by electroporation (see, e.g., Wong and Neumann, *Biochem. Biophys. Res. Commun.* 107:584-87 (1982)) and biolistics (e.g., a gene gun; Johnston and Tang, *Methods Cell Biol.* 43 Pt A:353-65 (1994); Fynan et al., *Proc. Natl. Acad. Sci. USA* 90:11478-82 (1993)).

In certain embodiments, a hepsin transgene can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-hosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., *Med. Chem.* 42:4292-99 (1999); Godbey et al., *Gene Ther.* 6:1380-88 (1999); Kichler et al., *Gene Ther.* 5:855-60 (1998); Birchaa et al., *J. Pharm.* 183:195-207 (1999); each incorporated by reference herein in its entirety.)

In some embodiments, a hepsin transgene can be microinjected into pronuclei of fertilized oocytes or the nuclei of ES cells. A typical method is microinjection of the fertilized oocyte. The fertilized oocytes are microinjected with nucleic acids encoding hepsin by standard techniques. The microinjected oocytes are typically cultured in vitro until a "pre-implantation embryo" is obtained. Such a pre-implantation embryo can contain approximately 16 to 150 cells. Methods for culturing fertilized oocytes to the pre-implantation stage include those described by Gordon et al. (*Methods in Enzymology* 101:414 (1984)); Hogan et al. (in *Manipulating the Mouse Embryo*, Cold Spring Harbor Laboratory Press, Cold Spring Harbor, N.Y. (1986)); Hammer et al. (*Nature* 315:680 (1986)); Gandolfi et al. (*J. Reprod. Fert.* 81:23-28 (1987)); Rexroad et al. (*J. Anim. Sci.* 66:947-53 (1988)); Eyestone et al. (*J. Reprod. Fert.* 85:715-20 (1989)); Camous et al. (*J. Reprod. Fert.* 72:779-85 (1989)); and Heyman et al. (*Theriogenology* 27:5968 (1989)) for mice, rabbits, pigs, cows, and the like. (These references are incorporated herein in their entirety.) Such pre-implantation embryos can be thereafter transferred to an appropriate (e.g., pseudopregnant) female. Depending upon the stage of development when the hepsin transgene, or a hepsin transgene-containing cell is introduced into the embryo, a chimeric or mosaic animal can result. Mosaic and chimeric animals can be bred to form true germline transgenic animals by selective breeding methods. Alternatively, microinjected or transfected embryonic stem cells can be injected into appropriate blastocysts and then the blastocysts are implanted into the appropriate foster females (e.g., pseudopregnant females).

A hepsin transgene also can be introduced into cells by infection of cells or into cells of a zygote with an infectious virus containing the mutant gene. Suitable viruses include retroviruses (see generally Jaenisch, *Proc. Natl. Acad. Sci. USA* 73:1260-64 (1976)); defective or attenuated retroviral vectors (see, e.g., U.S. Pat. No. 4,980,286; Miller et al., *Meth. Enzymol.* 217:581-99 (1993); Boesen et al., *Biotherapy* 6:291-302 (1994); these references are incorporated herein in their entirety), lentiviral vectors (see, e.g., Naldini et al., *Science* 272:263-67 (1996), incorporated by reference herein in its entirety), adenoviruses or adeno-associated virus (AAV) (see, e.g., Ali et al., *Gene Therapy* 1:367-84 (1994); U.S. Pat. Nos. 4,797,368 and 5,139,941; Walsh et al., *Proc. Soc. Exp. Biol. Med.* 204:289-300 (1993); Grimm et al., *Human Gene Therapy* 10:2445-50 (1999); the disclosures of which are incorporated by reference herein in their entirety).

Viral vectors can be introduced into, for example, embryonic stem cells, primordial germ cells, oocytes, eggs, spermatocytes, sperm cells, fertilized eggs, zygotes, blastomeres, or any other suitable target cell. In an exemplary embodiment, retroviral vectors which transduce dividing cells (e.g., vectors derived from murine leukemia virus; see, e.g., Miller and Baltimore, *Mol. Cell. Biol.* 6:2895 (1986)) can be used. The production of a recombinant retroviral vector carrying a gene of interest is typically achieved in two stages. First, a hepsin transgene can be inserted into a retroviral vector which contains the sequences necessary for the efficient expression of the hepsin transgene (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (–PBS), a 3' regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant vector, the vector DNA is introduced into a packaging cell line. Packaging cell lines provide viral proteins required in trans for the packaging of viral genomic RNA into viral particles having the desired host range (e.g., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permits entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Oocytes which have not undergone the final stages of gametogenesis are typically infected with the retroviral vector. The injected oocytes are then permitted to complete maturation with the accompanying meiotic divisions. The breakdown of the nuclear envelope during meiosis permits the integration of the proviral form of the retrovirus vector into the genome of the oocyte. When pre-maturation oocytes are used, the injected oocytes are then cultured in vitro under conditions that permit maturation of the oocyte prior to fertilization in vitro. Oocytes can be matured in vivo and employed in place of oocytes matured in vitro. Methods for the superovulation and collection of in vivo matured (e.g., oocytes at the metaphase 2 stage) oocytes are known for a variety of mammals (e.g., for superovulation of mice, see Hogan et al., in *Manipulating the Mouse Embryo: A Laboratory Manual,* 2nd ed., Cold Spring Harbor Laboratory Press, Cold Spring Harbor, N.Y. (1994), pp. 130-133; the disclosure of which is incorporated by reference herein in its entirety).

In some embodiments, a transgenic animal is prepared by nuclear transfer. The terms "nuclear transfer" or "nuclear transplantation" refer to methods of preparing transgenic animals wherein the nucleus from a donor cell is transplanted into an enucleated oocyte. Nuclear transfer techniques or nuclear transplantation techniques are known in the art. (See, e.g., Campbell et al., *Theriogenology* 43:181 (1995); Collas and Barnes, *Mol. Reprod. Dev.* 38:264-67 (1994); Keefer et al., *Biol. Reprod.* 50:935-39 (1994); Sims et al., *Proc. Natl. Acad. Sci. USA* 90:6143-47 (1993); Prather et al., *Biol. Reprod.* 37:59-86 (1988); Roble et al., *J. Anim. Sci.* 64:642-64 (1987); International Patent Publications WO 90/03432, WO 94/24274, and WO 94/26884; U.S. Pat. Nos. 4,994,384 and 5,057,420; the disclosures of which are incorporated by reference herein in their entirety.) For example, nuclei of transgenic embryos, pluripotent cells, totipotent cells, embryonic stem cells, germ cells, fetal cells or adult cells (i.e., containing a hepsin transgene) can be transplanted into enucleated oocytes, each of which is thereafter cultured to the blastocyst stage. (As used herein, the term "enucleated" refers to cells from which the nucleus has been removed as well as to cells in which the nucleus has been rendered functionally inactive.) The nucleus containing a hepsin transgene can be introduced into these cells by any suitable method. The transgenic cell is then typically cultured in vitro to the form a pre-implantation embryo, which can be implanted in a suitable female (e.g., a pseudo-pregnant female).

The transgenic embryos optionally can be subjected, or resubjected, to another round of nuclear transplantation. Additional rounds of nuclear transplantation cloning can be useful when the original transferred nucleus is from an adult cell (e.g., fibroblasts or other highly or terminally differentiated cell) to produce healthy transgenic animals.

Other methods for producing a transgenic animal expressing a hepsin transgene include the use male sperm cells to carry the hepsin transgene to an egg. In one example, a hepsin transgene can be administered to a male animal's testis in vivo by direct delivery. The hepsin transgene can be introduced into the seminiferous tubules, into the rete testis, into the vas efferens or vasa efferentia, using, for example, a micropipette.

In some embodiments, a hepsin transgene can be introduced ex vivo into the genome of male germ cells. A number of known gene delivery methods can be used for the uptake of nucleic acid sequences into the cell. Suitable methods for introducing a hepsin transgene into male germ cells include, for example, liposomes, retroviral vectors, adenoviral vectors, adenovirus-enhanced gene delivery systems, or combinations thereof.

Following transfer of a hepsin transgene into male germ cells, a transgenic zygote can be formed by breeding the male animal with a female animal. The transgenic zygote can be formed, for example, by natural mating (e.g., copulation by the male and female vertebrates of the same species), or by in vitro or in vivo artificial means. Suitable artificial means include, but are not limited to, artificial insemination, in vitro fertilization (IVF) and/or other artificial reproductive technologies, such as intracytoplasmic sperm injection (ICSI), subzonal insemination (SUZI), partial zona dissection (PZD), and the like, as will be appreciated by the skilled artisan. (See, e.g., International Patent Publication WO 00/09674, the disclosure of which is incorporated by reference herein in its entirety.)

A variety of methods can be used to detect the presence of a hepsin transgene in target cells and/or transgenic animals. Since the frequency of transgene incorporation can be low, although reliable, the detection of transgene integration in the pre-implantation embryo can be desirable. In one aspect, embryos are screened to permit the identification of hepsin-transgene-containing embryos for implantation to form transgenic animals. For example, one or more cells are removed from the pre-implantation embryo. When equal division of the embryo is used, the embryo is typically not cultivated past the morula stage (32 cells). Division of the pre-implantation embryo (see, e.g., Williams et al., *Theriogenology* 22:521-31 (1986)) results in two "hemi-embryos" (hemi-morula or hemi-blastocyst), one of which is capable of subsequent development after implantation into the appropriate female to develop in utero to term. Although equal division of the pre-implantation embryo is typical, it is to be understood that such an embryo can be unequally divided either intentionally or unintentionally into two hemi-embryos. Essentially, one of the embryos which is not analyzed usually has a sufficient cell number to develop to full term in utero. In a specific embodiment, the hemi-embryo (which is not analyzed), if shown to be transgenic, can be used to generate a clonal population of transgenic animals, such as by embryo splitting.

One of the hemi-embryos formed by division of pre-implantation embryos can be analyzed to determine if the hepsin transgene has integrated into the genome of the organism. Each of the other hemi-embryos can be maintained for subsequent implantation into a recipient female, typically of the same species. A typical method for detecting a hepsin transgene at this early stage in the embryo's development uses these hemi-embryos in connection with allele-specific PCR, which can differentiate between a hepsin transgene and an endogenous transgene. (See, e.g., McPherson et al. (eds) *PCR2: A Practical Approach,* Oxford University Press (1995); Cha et al., *PCR Methods Appl.* 2:14-20 (1992); the disclosures of which are incorporated by reference herein.)

After a hemi-embryo is identified as a transgenic hemi-embryo, it optionally can be cloned. Such embryo cloning can be performed by several different approaches. In one cloning method, the transgenic hemi-embryo can be cultured in the same or in a similar media as used to culture individual oocytes to the pre-implantation stage. The "transgenic embryo" so formed (typically a transgenic morula) can then be divided into "transgenic hemi-embryos" which can be implanted into a recipient female to form a clonal population of two transgenic non-human animals. Alternatively, the two transgenic hemi-embryos obtained can be again cultivated to the pre-implantation stage, divided, and recultivated to the transgenic embryo stage. This procedure can be repeated until the desired number of clonal transgenic embryos having the same genotype are obtained. Such transgenic embryos can then be implanted into recipient females to produce a clonal population of transgenic non-human animals.

In addition to the foregoing methods for detecting the presence of a hepsin transgene, other methods can be used. Such methods include, for example, in utero and postpartum analysis of tissue. In utero analysis can be performed by several techniques. In one example, transvaginal puncture of the amniotic cavity is performed under echoscopic guidance (see, e.g., Bowgso et al., *Bet. Res.* 96:124-27 (1975); Rumsey et al., *J. Anim. Sci.* 39:386-91 (1974)). This involves recovering amniotic fluid during gestation. Most of the cells in the amniotic fluid are dead. Such cells, however, contain genomic DNA which can be subjected to analysis (e.g., by PCR) for the hepsin transgene as an indication of a successful transgenesis. Alternatively, fetal cells can be recovered by chorion puncture. This method also can be performed transvaginally and under echoscopic guidance. In this method, a needle can be used to puncture the recipient animal's placenta, particularly the placentonal structures, which are fixed against the vaginal wall. Chorion cells, if necessary, can be separated from maternal tissue and subjected to PCR analysis for the hepsin transgene as an indication of successful transgenesis.

The presence of a hepsin transgene also can be detected after birth. In such cases, the presence of a hepsin transgene can be detected by taking an appropriate tissue biopsy, such as from an ear or tail of the putative transgenic animal. The presence of a hepsin transgene can also be detected by assaying for expression of the hepsin transgene polypeptide in a tissue.

The location and number of integration events can be determined by methods known to the skilled artisan. (See, e.g., Ausubel et al., supra; Sambrook et al., supra.) For example, PCR or Southern blot analysis of genomic DNA extracted from infected oocytes and/or the resulting embryos, offspring and tissues derived therefrom, can be employed when information concerning the site of integration of the viral DNA into the host genome is desired. To examine the number of integration sites present in the host genome, the extracted genomic DNA can typically be digested with a restriction enzyme which cuts at least once within the vector sequences. If the enzyme chosen cuts twice within the vector sequences, a band of known (i.e., predictable) size is generated in addition to two fragments of novel length which can be detected using appropriate probes.

Clones of the non-human transgenic animals described herein can also be produced according to the methods described in Wilmut et al., *Nature* 385:810-813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Other methods of preparing transgenic animals are disclosed, for example, in U.S. Pat. Nos. 5,633,076 or 6,080,912; and in International Patent Publications WO 97/47739, WO 99/37143, WO 00/75300, WO 00/56932, and WO 00/08132, the disclosures of which are incorporated herein by reference in their entirety.

A transgenic animal containing a hepsin transgene can used as a founder animal breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In a related aspect, a non-human transgenic animal overexpressing a hepsin transgene can be a source of cells to establish cell lines expressing or overexpressing the hepsin transgene. For example, cell lines can be derived from mice that overexpress a mouse or cognate, heterologous hepsin transgene.

The hepsin transgene is overexpressed in a non-human animal cancer model. As used herein, "non-human animal cancer model" refers to an animal exhibiting uncontrolled cellular growth in one or more tissues or organs leading to the formation of precancerous lesions and/or cancer that result in tumor formation. A non-human animal cancer model can exhibit, for example, hyperplasia, dysplasia, in situ carcinoma, invasive cancer neoplasia and/or metastatic cancer The non-human, animal cancer model typically has genetic predisposition for developing a precancerous, cancerous or other hyperplastic condition. The genetic predisposition can be associated with, for example, the presence of one or more mutations of the animal, the introduction of a transgene into genome of the animal, or the like. Suitable animals models include those for prostatic intraepithelial neoplasia, prostate, ovarian, kidney and liver cancers. Mouse prostate cancer transgenic models include, for example, LPB-Tag mice (Kasper et al., 1998), MYC mice (Ellwood-Yen et al., *Cancer Cell.* 4:233-38 (2003)), BCL2 mice, TRAMP mice (Greenberg, *Proc. Natl. Acad. Sci. USA* 92:3439-43 (1995)), FGF8b mice, and dominant-negative TGFbeta (Matusik et al., "Transgenic mouse models of prostate cancer," in: *Transgenics in Endocrinology*, ed. by M M Matzuk, C W Brown, and T R Kumar, The Humana Press Inc (Totowa, N.J.) Chapter 19, pp 401-425 (2001); Shappell et al., *Cancer Res.* 64:2270-2305 (2004)). Mouse prostate cancer knockout models include, for example, Nkx3.1 null mice, p27 null mice, PTEN heterozygous and prostate-specific null mice (Huss et al., *Semin Cancer Biol.* 11:245-260 (2001); Wang et al., *Cancer Cell* 4:209 (2003)). Mouse ovarian cancer models include, for example, mice obtained using the ex vivo introduction of c-myc, K-ras or Akt genes into the somatic ovarian cells of adult mice (Orsulic et al., 2002), inhibin transgenic mice (Matzuk et. al., *Nature* 360:313-319 (1992)), LN transgenic mice (Nilson et al., *Recent Prog. Horm. Res.* 55:69-89 (2000); Keri et al., *Proc. Natl. Acad. Sci. USA* 97:383-387 (2000), FORCO mice (Danilovich et al., *Endocrinology* 142:3673-3684 (2001)), Bcl2 mice (Hsu et al., *Endocrinology* 137(11): 4837-43 (1996)), leuteinizing hormone transgenic mice (Risma et al., *Proc. Natl. Acad. Sci. USA* 92:1322-1326 (1995)), SV40 T antigen mice (Rahman et al., (*Mol. Cell Endocrinol.* 145:167-174 (1998)); Dutertre et al., *Endocrinology* 142:4040-4046 (2001)), Wx/Wv mice (Murphy, *J. Natl. Cancer Inst.* 48:1283-1295 (1972)); Murphy and Beamer, *Cancer Res.* 33:721-723 (1973)), Sl/Slt germ cell deficient mice (Ishimura et al., *Arch. Histol. Jpn.* 49:379-389 (1986)), gcd/gcd animals (Duncan and Chada, *J. Comp. Pathol.* 109:13-19 (1993)). A rat model of kidney cancer include, for example, Eker rat model of hereditary renal carcinoma, Nihon rat (Hino et al., *Cancer Sci.* 94(2):142-7 (2003)). The mouse models of liver cancer include, for example, the Hepatitis B and C virus transgenic mice (Rogers and Fox, *Am. J. Physiol. Gastrointest. Liver. Physiol.* 286(3): G361-6 (2004)), TGF alpha transgenic mice, and Bcl2 transgenic mice (Fausto, *Semin Liver Dis.* 19(3):243-52 (1999)).

In certain embodiments, the animal model exhibits a low level of metastasis, as compared with the human or other animal counterpart, for which the animal model is correlated. In such animal models, tumor development, progression and/or metastasis can be enhanced or increased by expression or overexpression of a hepsin transgene, as compared with an animal model not expressing or overexpressing the hepsin transgene. In some embodiments, production of hepsin will be significantly higher, typically being at least two-fold higher, at least five-fold higher, at least ten-fold higher, or at least 10-20-fold higher, as a compared with a control animal. In some embodiments, overexpression of the hepsin transgene can be detected as an increased propensity of the animal model to develop metastases (infra).

A hepsin transgene can be introduced into a non-human animal cancer model by, for example, breeding a male animal with a female animal (e.g., natural mating) or by in vitro or in vivo artificial means (see supra). Over-expression of a hepsin transgene into an animal model of cancer results in generation of an animal that develop rapid metastasis. The resulting animal can be used, for example, for modeling of human cancer progression, metastasis and/or testing the efficacy of the test compounds (e.g., drug candidates) for treatment of cancer or other hyperplastic condition.

In some embodiments, an animal cancer model can be constructed, for example, by implanting precancerous or cancerous cell lines into an animal. Such an animal model may or may not have a genetic predisposition to cancer. Prior to implantation, a hepsin transgene(s) can be introduced into the precancerous or cancerous cell line. Suitable cells lines include, for example, PC3 and DU145 for prostate cancer.

The cell lines can be implanted, for example, into 6-week-old nude female mice. The cells can be injected into a subcutaneous space in the flank of the animal. The nude mice are sacrificed to harvest the tumor fragments 3 weeks after tumor cell injection. These tumor fragments can then be used for surgical implantation into the corresponding tissue (surgical orthotopic implantation (SOI)) in nude mice as recipients.

The recipient mice can be implanted with fragments of the subcutaneously grown colon cancer, lung cancer, breast cancer, prostate cancer or melanoma. The size of the fragment can be, for example, about 1 mm$^3$. For prostate cancer, an opening can be made above the pubic symphysis to expose the prostate gland. The fascia surrounding the dorsal portion of the prostate and the dorsal lateral lobes of the gland are separated by a small incision. Fragments can be sutured into the incision and the incision closed. The animal can be allowed to recover. For other cancers, incisions can be made in the appropriate tissue or organ.

Transgenic animal models overexpressing a hepsin transgene can be used to assay test compounds (e.g., a drug candidate) for efficacy on cancer development, progression and/or metastasis in test animals, or in samples or specimens (e.g., a biopsy) from the test animals. In some cases, it will be advantageous to measure the markers of cancer progression or metastasis in samples, blood, which may be obtained from the test animal without sacrifice of the animal.

Generally, the effect of a compound(s) on a test animal is compared with a test animal in the absence of test compound(s). In cases where the animal is sacrificed, a baseline can be established based on an average or a typical value from a control animal(s) that have not received the administration of any test compounds or any other substances expected to affect cancer progression and/or metastasis. Once such a baseline is determined, test compounds can be administered to additional test animals, where deviation from the baseline indicates that the test compound had an effect on cancer progression or metastasis. Test compounds which are considered positive, i.e., likely to be beneficial in the treatment of cancer, will be those which are able to reduce cancer progression and/or metastasis.

The test compounds can be any molecule, compound, or other substance which can be administered to a test animal. In some cases, the test compound does not substantially interfere with animal viability. Suitable test compounds may be small molecules, biological polymers, such as polypeptides, polysaccharides, polynucleotides, and the like. The test compounds will typically be administered to the animal at a dosage of from 1 ng/kg to 10 mg/kg, usually from 10 µg/kg to 1 mg/kg. Test compounds can be identified that are therapeutically effective, such as anti-proliferative agents, or as lead compounds for drug development.

In some embodiments, test compounds can be from diversity libraries, such as random or combinatorial peptide or non-peptide libraries. Many libraries are known in the art, such as, for example, chemically synthesized libraries, recombinant phage display libraries, and in vitro translation-based libraries.

Examples of chemically synthesized libraries are described in Fodor et al. (*Science* 251:767-73 (1991)), Houghten et al. (*Nature* 354:84-86 (1991)), Lam et al. (*Nature* 354:82-84 (1991)), Medynski (*Bio/Technology* 12:709-10 (1994)), Gallop et al. (*J. Med. Chem.* 37:1233-51 (1994)), Ohlmeyer et al. (*Proc. Natl. Acad. Sci. USA* 90:10922-26 (1993)), Erb et al. (*Proc. Natl. Acad. Sci. USA* 91:11422-26 (1994)), Houghten et al. (*Biotechniques* 13:412-21 (1992)), Jayawickreme et al. (*Proc. Natl. Acad. Sci. USA* 91:1614-18 (1994)), Salmon et al. (*Proc. Natl. Acad. Sci. USA* 90:11708-12 (1993)), International Patent Publication WO 93/20242, and Brenner and Lerner (*Proc. Natl. Acad. Sci. USA* 89:5381-83 (1992)).

Examples of phage display libraries are described in Scott and Smith (*Science* 249:386-90 (1990)), Devlin et al. (*Science* 249:404-06 (1990)), Christian et al. (*J. Mol. Biol.* 227: 711-18 (1992)), Lenstra (*J. Immunol. Meth.* 152:149-57 (1992)), Kay et al. (*Gene* 128:59-65 (1993)), and International Patent Publication WO 94/18318.

In vitro translation-based libraries include, but are not limited to, those described in International Patent Publication WO 91/05058, and Mattheakis et al. (*Proc. Natl. Acad. Sci. USA* 91:9022-26 (1994)). By way of examples of nonpeptide libraries, a benzodiazepine library (see, e.g., Bunin et al., *Proc. Natl. Acad. Sci. USA* 91:4708-12 (1994)) can be adapted for use. Peptide libraries (see, e.g., Simon et al., *Proc. Natl. Acad. Sci. USA* 89:9367-71(1992)) can also be used. Another example of a library that can be used, in which the amide functionalities in peptides have been permethylated to generate a chemically transformed combinatorial library, is described by Ostresh et al. (*Proc. Natl. Acad. Sci. USA* 91:11138-42 (1994)).

The following examples are provided merely as illustrative of various aspects of the invention and shall not be construed to limit the invention in any way.

EXAMPLES

To determine the role of hepsin in prostate epithelium in vivo, transgenic mice having a probasin promoter driven hepsin gene (PB-hepsin) were generated and analyzed. Hepsin overexpression caused weakening of epithelial-stromal adhesion. Immunofluorescent staining and electron microscopy revealed the disorganization and disruption of the basement membrane in hepsin-expressing prostate glands. To determine the potential role of hepsin in prostate cancer progression, PB-hepsin transgenic animals were crossed with mice expressing the SV40 large T antigen in the prostate epithelium (LPB-Tag mice, line 12T-7f) (Kasper et al., *Lab. Invest.* 78:319-333 (1998)). LPB-Tag animals develop PIN lesions and foci of prostate carcinoma; however, primary tumors do not metastasize. By 21 weeks of age, up to 65% of the double transgenic LPB-Tag/PB-hepsin mice, but none of the single transgenic LPB-Tag or PB-hepsin animals, developed prostate cancer which metastasizes to liver, lung and bone. These data indicate that hepsin promotes primary prostate cancer progression and metastasis in the LBP-Tag mouse model of prostate cancer.

Procedures

Plasmids

Generation of PB-IRES-hrGFP transgenic construct: The ARR2PB synthetic probasin promoter (Zhang et al., 2000) was KpnI(blunted)/SacI digested and subcloned into the NsiI (blunted) and SacI sites of the pIRES-hrGFP-2a vector (Stratagene). The β-globin intron sequence from the K14 expression construct (Vasioukhin et al., *Proc. Natl. Acad. Sci. USA* 96:8551-8556 (1999)) was AvaI(blunted)/NotI digested and subcloned into the SpeI (blunted) and NotI sites of the ARR$_2$PB-pIRES-hrGFP-2a backbone. The MCS in the pBluescript II KS vector (Stratagene) was modified by SacI/PstI digestion and ligation of oligos encoding the MluI and AscI sites. The ARR2PB-β-globin-hrGFP-2a-SV40 poly A fragment was ClaI/MluI (partial) digested and subcloned into the ClaI and MluI sites of the modified pBluescript vector. The resulting PB-IRES-hrGFP vector contained the ARR$_2$PB promoter to direct expression to prostate epithelium, the β-globin intron to increase the levels of the transcript, the multiple cloning site with unique SpeI, NotI, SrfI, XmaI, EcoRI and SphI cleavage sites for cloning the desired insert, the IRES-hrGFP sequences to reinitiate the translation of the reporter hrGFP from the same transcript and the SV40 polyadenylation sequence to stabilize the mRNA.

Generation of the PB-hepsin transgenic construct. The full-length mouse hepsin cDNA was PCR-amplified from the IMAGE clone #747832 using the primers containing the SpeI and EcoRI sites (5'-GCACTAGTATGGCGAAG-GAGGGTGGCC-3' (SEQ ID NO:1) and 5'-GCGAATTCT-CAGGGCTGAGTCACCATG-3' (SEQ ID NO:2)). The resulting 1.25 kB fragment was cloned into the SpeI and EcoRI sites of the PB-IRES-hrGFP vector. The PCR-generated hepsin cDNA was verified by sequencing.

Mice

The PB-hepsin fragment was obtained by ClaI/AscI digestion, purified and injected into fertilized C57BL/6JxCBA mouse eggs. The eggs were transplanted into pseudopregnant females (at the Fred Hutchinson Cancer Research Center (FHCRC) transgenic facility). The resulting mice were screened by PCR with primers used for amplification of the hepsin cDNA in the PB-hepsin plasmid construct (see above). Founder PB-hepsin mice were bred with C57BL/6J animals and the resulting lines were maintained on the C57BL/6J genetic background.

The LPB-Tag mice (line 12-T7f) have been previously described (Kasper et al, 1998). This transgenic line was maintained by breeding with CD-1 animals. LPB-Tag/PB-hepsin double transgenic mice were generated by breeding LPB-Tag females with PB-hepsin males. The resulting double transgenic males were analyzed at 21 weeks of age.

Mouse Dissection, Internal Organs, GFP Imaging, Histology and Electron Microscopy Mice were dissected using the Zeiss SV11 dissecting scope equipped with a Green Fluorescent Protein (GFP) attachment. The visible light and GFP images were captured using a Nikon digital camera. The ventral, dorsal, and lateral prostate lobes were dissected and fixed in 4% formaldehyde, processed and embedded in paraffin. Sections (5 μM) were stained with hematoxylin and eosin, examined and photographed using a Nikon TE 200 microscope. To study metastasis formation, the liver, lung, kidney, spleen and femur bone were analyzed. For transmission electron microscopy (EM), samples were fixed in 2% glutaraldehyde, 4% formaldehyde in 0.05M sodium cacodylate buffer at 4° C. overnight and processed for Epon embedding. Samples were visualized with a JEOL 1010 microscope.

Northern, Western Blot and RT-PCR Analyses and In Situ Hybridization.

Northern and Western blot analyses were carried out according to standard protocols (Sambrook and Russell, 2001). Total RNA was extracted using the Trizol reagent from Gibco. PCR-generated full-length mouse hepsin cDNA and GAPDH probes were used as probes for Northern blot analysis. In situ hybridization was performed on paraffin sections as described previously (Fijnvandraat et al., 2002). The digoxygenin-labeled antisense hrGFP RNA was synthesized using the kit from Roche. The RT-PCR analyses were performed using the kit from Invitrogen. Primers 5'-AGGAGAT-CATGAGCTTCAAGG-3' (SEQ ID NO:3) and 5'-GCTGTA-GAACTTGCCGCTGT-3' (SEQ ID NO:4) were used to amplify the transgenic transcript. Primers 5'-CATGTGGGC-CATGAGGTCCACCAC-3' (SEQ ID NO:5) and 5'-TGAAG-GTCGGAGTCAACGGATTTGGT-3' (SEQ ID NO:6) were used to amplify the GAPDH transcript.

Immunofluorescence and Immunohistochemistry

For immunofluorescent staining, tissues were embedded in OCT and then frozen immediately on dry ice. The 7 μm cryosections were subjected to indirect immunostaining and analyzed using the Nikon TE 200 microscope equipped with COOLSNAP HQ digital camera or using the Applied Precision, Inc. Delta vision SA3.1 Deconvolution Microscope. In some cases tissues were first processed, embedded in paraffin, sectioned and resulting sections were deparafinized, rehydrated and processed as described above. The ABC elite or ABC MOM kits (Vector laboratories) were used for immunohistochemistry. Antibodies were detected with a DAB peroxidase substrate kit and sections were counterstained with hematoxylin QS (both from Vector laboratories).

Antibodies and Apoptosis Staining

Antibodies used: anti-hepsin (Cayman Chemical), anti-Collagen I and III (Rockland), anti-β-actin (Sigma), anti-Laminin 5 (β3/γ2 chains), anti-Laminin 1(β1/γ1 chains), anti-fibronectin, anti-β4-integrin (Dr. William Carter, FHCRC), anti-Ki67 (Novacastra Laboratories), anti-keratin 8, anti-Collagen IV (Developmental Studies Hybridoma Bank), anti-keratin 5 (Vasioukhin et al., 2001), anti-synaptophysin (Zymed Laboratories), anti-SV40 T-Ag (Oncogene Research Products), and anti-androgen receptor (N-20, Santa Cruz Biotechnology). Relevant FITC- or Texas Red-conjugated donkey or goat antibodies (Jackson Laboratories) were used for detection of primary antibodies. Apoptosis was determined using the FragEL kit from Oncogene Research.

Quantitation of Cell Differentiation, Proliferation and Apoptosis

For quantitation of data obtained using the immunofluorescent stainings similar areas in the prostates of the PB-hepsin, LPB-Tag, PB-hepsin/LPB-Tag and wild-type animals were selected and total number of cells and cells stained positive with indicated antibodies were counted.

Statistical Analysis

Fisher's exact test was used to compare the metastases data between the LPB-Tag and LPB-Tag/PB-hepsin animals.

Results

Generation of Transgenic Mice Expressing Hepsin in Prostate Epithelium

Figure 1:
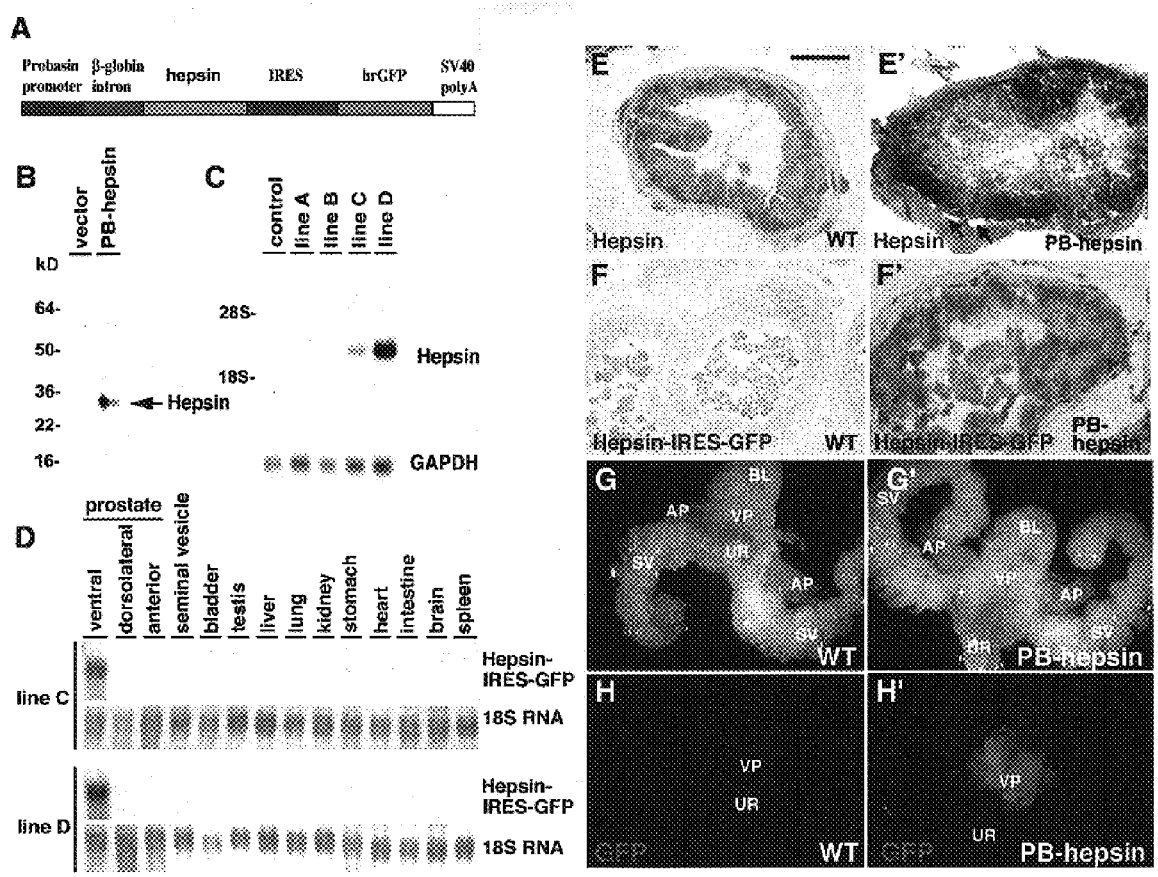
FIG. 1. Generation of transgenic mice overexpressing hepsin in prostate epithelium. A: Schematic representation of probasin-hepsin (PB-hepsin) transgene. B: The PB-hepsin transgenic construct produces hepsin protein in a prostate carcinoma cell line. The empty vector or PB-hepsin construct were transiently transfected into LNCaP cells and total protein extracts were analyzed by Western blot with anti-hepsin antibodies. C: The PB-hepsin transgenic mouse lines C and D express hepsin mRNA in the prostate gland. Total RNA was extracted from the prostate glands of 10 week-old control (control) and transgenic (lines A-D) mice and analyzed by Northern blot hybridization using hepsin (Hepsin) and GAPDH (GAPDH) probes. D: Ventral prostate-specific expression of the PB-hepsin transgene. Total RNA was extracted from indicated prostate lobes and organs of 21 week-old PB-hepsin animals ("line C" and "line D") and analyzed by Northern blot hybridization with GFP (Hepsin-IRES-GFP) and 18S RNA probes. E-E': Immunohistochemical staining of 14 week-old wild-type (WT) and PB-hepsin (PB-hepsin) prostate glands with anti-hepsin antibodies. Arrows indicate areas of separation between the epithelial and stromal cell compartment. F-F': In situ hybridization of ventral prostates from the 14 week-old animals with antisense hrGFP probe. G-H': Macroscopic appearance and GFP-imaging of selected urogenital organs from wild-type and PB-hepsin animals. Bladders (BL) with urethras (UR), seminal vesicles (SV), anterior (AP), ventral (VP) prostate lobes were dissected from 20 week-old wildtype (G, H) and PB-hepsin (G', H') animals. The organs were visualized using visible light (G, G') and GFP fluorescence (H, H'). Note prominent GFP fluorescence in the ventral prostate lobes of PB-hepsin mice. Bar in E represents 55 µm in E-F'.

The modified probasin promoter ($ARR_2PB$) is specifically active in prostate epithelial cells in vivo and in vitro and was used for prostate-specific expression of hepsin (Zhang et al., 2000). In addition to the promoter, the transgenic construct contains the β-globin intron, full-length mouse hepsin cDNA, internal ribosome entrance site (IRES) and humanized renilla GFP (hrGFP) cDNA sequences (FIG. 1A). This configuration directs the expression of hepsin and hrGFP proteins from the same transcript allowing for convenient monitoring of transcription specificity by whole-mount internal organ GFP detection (FIG. 1G-H').

To confirm the functionality of the transgenic construct, LNCaP human prostate carcinoma cells were transiently transfected with the probasin-hepsin (PB-hepsin) plasmid. Western blot analysis of total protein extract from hepsin transfected cells, using anti-hepsin antibodies revealed a 31-kD band corresponding to the heavy chain of proteolytically processed hepsin (FIG. 1B). Four mouse lines transmitting the PB-hepsin transgene were generated and analyzed. Northern blot hybridization with hepsin probe revealed that only two lines (C and D) expressed the transgene (FIG. 1C). The expression of the transgene was restricted to the ventral lobe of the prostate gland and it was not detectable in other organs and tissues (FIG. 1D). Similar data were obtained using RT-PCR analysis (3 animals were analyzed for each line). Endogenous hepsin expression was not detected in the prostates of wild-type 10 week-old animals. Because endogenous hepsin expression was not detected, the correlation of hepsin in the transgenic animals with the levels of hepsin in human prostate cancer, where hepsin transcripts are upregulated up to 34-fold in comparison to normal tissue (Stamey et al., 2001), could not be estimated.

Immunohistochemical staining with anti-hepsin antibodies (n=2) and in situ hybridization with an antisense GFP probe (n=3) demonstrated prostate epithelial cell specific expression of the transgene (FIGS. 1E-F'). To establish whether the transgenic construct also expressed functional hrGFP protein, whole-mount internal organ GFP detection was performed using a dissecting microscope with GFP attachment (FIGS. 1G-H'). The hrGFP expression was readily detectable in the ventral lobe of prostate gland of the PB-hepsin animals (n>30). Although GFP fluorescence was visible by whole-mount organ GFP analysis, expression was too weak to be detected on frozen tissue sections. This enabled the use of the green channel for detection of other proteins in triple immunofluorescence staining during analysis of the PB-hepsin mice (see below).

Figure 2:
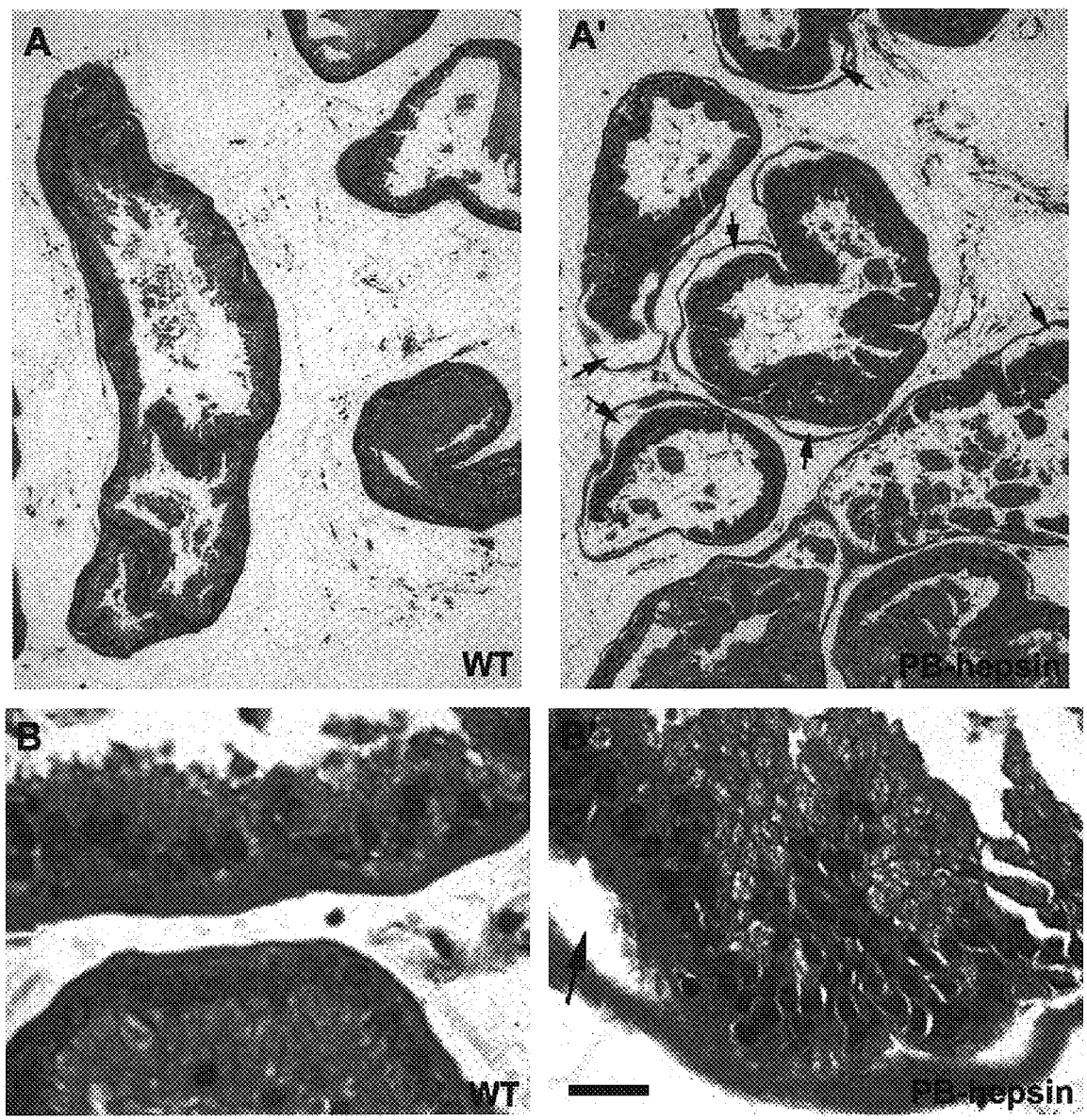
FIG. 2. Histologic appearance of ventral prostate lobes from control (WT) and PB-hepsin (PB-hepsin) animals. Tissue sections were stained with hematoxylin & eosin and examined using 10× (A, A') and 40× (B, B') objectives. Note separation between epithelial cells and the stromal layer in the PB-hepsin animals (arrows in A', B'). Bar in B' represents 120 µm in B, B'.

PB-Hepsin Transgenic Mice Undergo Normal Differentiation, Proliferation and Apoptosis, but Display Disorganization of the Basement Membrane Histologic examination of prostates from 3-4 month-old animals revealed no obvious abnormalities in the prostate glands of PB-hepsin transgenic mice. In contrast, 3 out of 4 one year-old PB-hepsin, but none of the control littermates (n=5), displayed separation between the epithelial and stromal cell layers (arrows in FIGS. 2A-B'). Small areas of separation between the epithelial and stromal cell layers were occasionally observed in the younger 14 week-old PB-hepsin mice (3 of 7 mice). These areas coincide with the epithelial fragments expressing high levels of hepsin (arrows in FIG. 1E'). While it is likely that separation was induced by the fixation and sectioning procedures, these results suggest a weakening of epithelial-stromal adhesion in the PB-hepsin animals.

Figure 3:
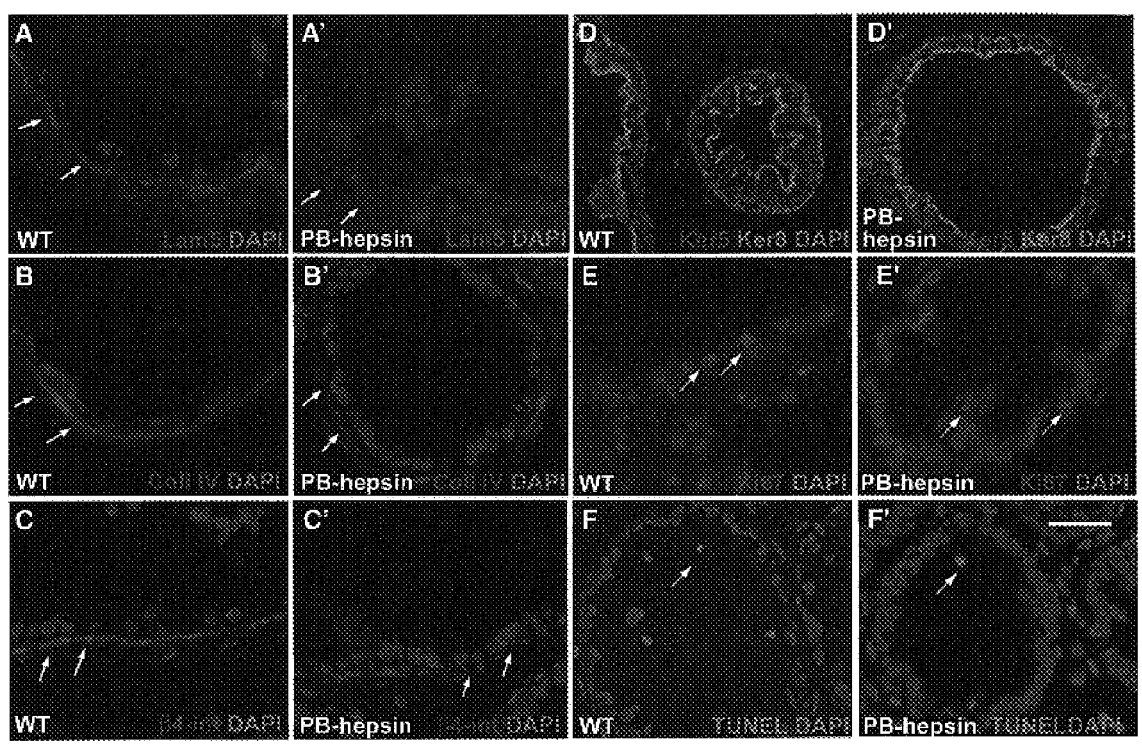
FIG. 3. Perturbation of the basement membrane, but maintenance of normal differentiation, proliferation and apoptosis in the prostate glands of PB-hepsin transgenic mice. Immunofluorescent staining of ventral prostate glands from 14 week-old wildtype (WT) and PB-hepsin (PB-hepsin) transgenic mice with anti-Laminin 5 (A, A'), anti-Collagen IV (B, B'), and anti-β4-integrin (C, C'), anti-keratin 5 (Ker5), shown in red; and anti-keratin 8 (Ker8), shown in green (D, D'), anti-Ki67 (Ki67) (E, E') antibodies and TUNEL staining for apoptotic cells (F, F'). White arrows in A-C' show position of the basement membrane. DAPI stained nuclei are shown in blue. The scale bar in F' represents 35 µm.

The epithelial and stromal cell compartments of the prostate are separated by the basement membrane, which is composed of numerous extracellular matrix proteins produced by both stromal and epithelial cells (Nagle et al., *Am. J. Pathol.* 146:1498-1507 (1995)). Since epithelial-stromal adhesion is compromised in PB-hepsin mice, localization of cell-substratum adhesion proteins was analyzed. This study utilized 4-5 month-old mice, a time point before the manifestation of the massive defects in epithelial-stromal adhesion observed in older animals. To analyze whether the expression of hepsin in transgenic mice affected the basement membrane, immunofluorescence staining was performed with antibodies against the basement membrane markers Laminin 5 (Laminin γ 2) and Collagen IV. In wild-type littermates, Laminin 5 staining appeared as a continuous line separating the stromal and epithelial cell compartments (arrows in FIG. 3A, n=5). In contrast, Laminin 5 staining in PB-hepsin transgenic mice appeared weak or completely absent (FIG. 3A', n=5). Antibodies against Collagen IV revealed disorganized and diffuse localization of this protein in PB-hepsin prostates (FIG. 3B', n=4). Although the basement membrane displayed normal focal staining, generally the staining appeared fragmented with large sections of the epithelial-stromal interface devoid of Collagen IV. This pattern of Laminin 5 and Collagen IV localization indicated a perturbation of the basement membrane in the PB-hepsin transgenic animals.

One of the major basement membrane receptors expressed in the prostate epithelium is α6β4-integrin, which is associated with hemidesmosomes. Expression of β4-integrin is decreased in human prostate carcinoma (Bonkhoff, *Anal. Quant. Cytol. Histol.* 20:437-442 (1998); Davis et al., *Prostate* 46:240-248 (2001); Murant et al., *Eur. J. Cancer* 33, 263-271 (1997)). Immunofluorescence staining with anti-β4-integrin antibodies revealed perturbation of the hemidesmosomal organization in the PB-hepsin prostates. Wild-type mice displayed a continuous line of β4-integrin staining along the basement membrane (arrows in FIG. 3C, n=5). In contrast, the β4-integrin staining in the transgenic prostate appeared as a discontinuous line (FIG. 3C', n=5), similar to the "beads on a string" appearance of β4-integrin in the skin of Laminin 5-deficient mice (Ryan et al., *J. Cell Biol.* 145: 1309-1323 (1999)). Taken together, the immunofluorescence staining with markers of the basement membrane and cell-substratum adhesion structures suggests that the integrity of the basement membrane is severely compromised in PB-hepsin transgenic animals.

Prostate epithelium contains two major cell populations: basal cells, which are characterized by the keratin 5/14 expression; and luminal cells, which are characterized by keratin 8/18 expression. To determine whether perturbation of the basement membrane in the PB-hepsin transgenic mice impacted normal prostate epithelial cell differentiation, immunofluorescent staining was performed with a variety of cell type specific markers. Staining with markers of basal and luminal cells revealed that both cell types are present in the PB-hepsin transgenic animals (FIG. 3D, D'). The basal cells represented 12.76±0.73% of total basal and luminal epithelial cells in the wild type (n=3) and 12.36%±1.64% in the PB-hepsin transgenic animals (n=3). Based on these observations, upregulation of hepsin in prostate epithelium did not lead to changes in cell differentiation.

Cell-substratum adhesion is important for regulation of cell proliferation and cell survival. While upregulation of hepsin had no impact on overall size of the prostate gland in the transgenic animals, it was necessary to determine whether hepsin causes differences in proliferation or cell death. To identify proliferating cells, immunostaining with anti-Ki67 antibody was performed. Only a very small proportion of epithelial cells (0.1-0.2%) were proliferating in control wild-type prostates (FIG. 3E, n=3). Upregulation of hepsin had no impact on the number of Ki67-positive cells (FIG. 3E', n=3).

To determine whether hepsin overexpression leads to changes in programmed cell death, TUNEL staining was performed (FIG. 3F, F'). Few epithelial cells in the wild-type prostate (0.02-0.05%) were TUNEL-positive and these were usually localized to the lumen of the prostatic acinus (n=3). The numbers and localization of apoptotic cells were similar in the PB-hepsin animals (n=3). Based on these observations, overexpression of hepsin in prostate epithelia did not lead to changes in cell proliferation or apoptotic cell death.

Figure 4:
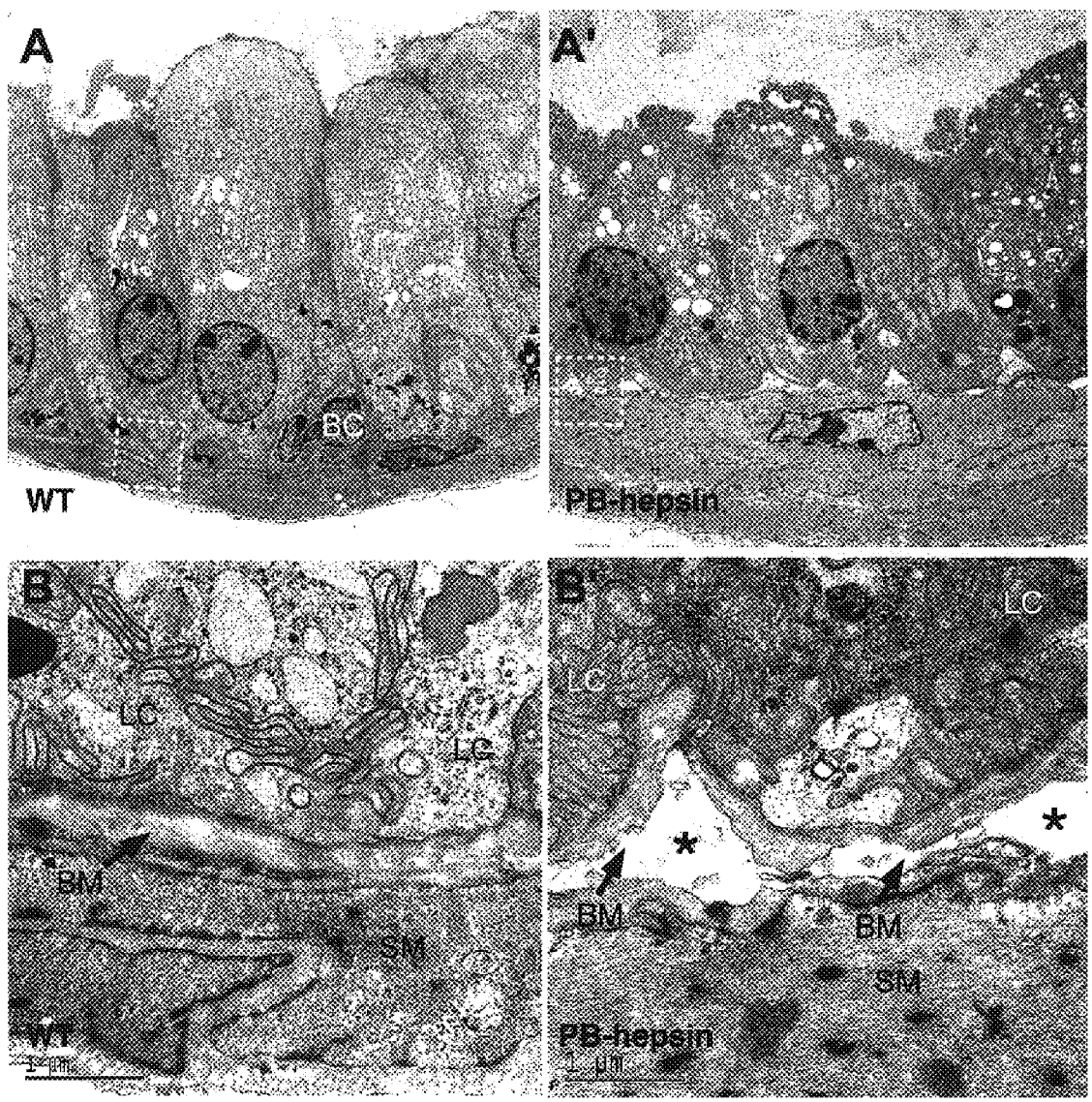
FIG. 4. Ultrastructural analysis of ventral prostates from 14 week-old male wildtype (A, B) and PB-hepsin (A', B') transgenic mice. Areas within the dashed square of A, A' are shown at higher magnification in B, B', respectively. The basement membrane in wild-type prostates is structurally intact and is tightly packed with collagen fibers (arrow in B). Transgenic prostates display microblisters at the basement membrane (shown with asterisk in B'). BM—basement membrane. SM—smooth muscle cell in the stromal cell compartment. LC—luminal cell. BC—basal cell. Bar in B' represents 1 µm in B, B', 7 µm in A, A'.

Ultrastructural Abnormalities in the Prostate Basement Membrane in PB-Hepsin Transgenic Animals To determine which part of the epithelial-stromal adhesion system is affected in hepsin-expressing prostates, 14 week-old transgenic animals were analyzed using transmission electron microscopy (FIGS. 4A-B'). Although the overall ultrastructure of prostates from PB-hepsin transgenic mice is similar to that of the wild-type controls, the organization of the basement membrane is consistently affected in the PB-hepsin animals (FIG. 4A'). The basement membrane in the wild-type animals contains tightly packed collagen fibers (FIG. 4B, n=2). Microblisters, separating the epithelial and stromal cell compartments are abundantly present in the transgenic animals. High magnification images of the blisters show disruption of the structure at the level of basement membrane (FIG. 4B', n=2). Collagen fibers were present in the basement membrane of PB-hepsin prostates; however, the adhesion between the fibers appears to be compromised. While it is likely that microblisters were induced by stress during fixation and sectioning procedures, the microblistering indicates a failure of proper adhesion between collagen fibers in the basement membrane of the PB-hepsin animals.

Hepsin Promotes Prostate Cancer Progression

In human prostate cancer progression, disruption of the basement membrane occurs during the transition from carcinoma in situ to invasive, metastasizing carcinoma (Abate-Shen and Shen, *Genes Dev.* 14:2410-2434 (2000)). To determine the significance of hepsin-mediated disruption of the basement membrane in prostate cancer, the LPB-Tag (Line 12T-7f) mouse model of prostate cancer (Kasper et al., 1998) was utilized. LPB-Tag mice express the SV40 large T antigen (Tag) under the control of the probasin promoter, which directs expression of the transgene specifically to the prostatic epithelium and accessory sex glands. The males of this transgenic line develop high-grade PIN and limited foci of adenocarcinoma at 20 weeks of age, but do not develop metastases. We first analyzed whether endogenous hepsin is upregulated in the prostate of the LPB-Tag animals. Northern blot analysis with a hepsin probe revealed no detectable endogenous hepsin expression in these animals (FIG. 5G, n=2).

To determine the role of hepsin in prostate cancer, double transgenic LPB-Tag/PB-hepsin mice were generated and analyzed. The LPB-Tag animals were crossed with the two independently generated lines of PB-hepsin mice (lines C and D), and double transgenic LPB-Tag/PB-hepsin males were analyzed at 21 weeks after birth. As previously reported, the LPB-Tag animals display massive enlargement of the prostate gland. The double transgenic LPB-Tag/PB-hepsin animals also showed enlargement of the prostate that was similar in size and weight to the prostates from LPB-Tag animals. Histologic examination of prostate glands from LPB-Tag animals revealed typical PIN-like lesions and stromal cell hyperplasia (FIGS. 5A, B, n=15). The prostate glands from the LPB-Tag/PB-hepsin animals display areas showing disruption and disorganization of epithelial structure (FIGS. 5A', B', n=26). In addition to PIN-like lesions, prostates from LPB-Tag/PB-hepsin double mutant mice typically showed adenocarcinoma with extensive glandular differentiation and focal areas of "punched-out", cribriform lesions. Often, the neoplastic glands invaded the periprostatic stroma (arrow in FIG. 5B'). In half of the analyzed double transgenic mice the tumor cells showed nuclear and chromatin patterns as well as architectural features including "rosette formation" that suggested neuroendocrine (NE) differentiation (arrowhead in FIG. 5B'). These changes were not due to the differences in the levels of SV40 T antigen, which were found to be similar between the LPB-Tag and LPB-Tag/PB-hepsin prostates (FIG. 5H).

Figure 5:
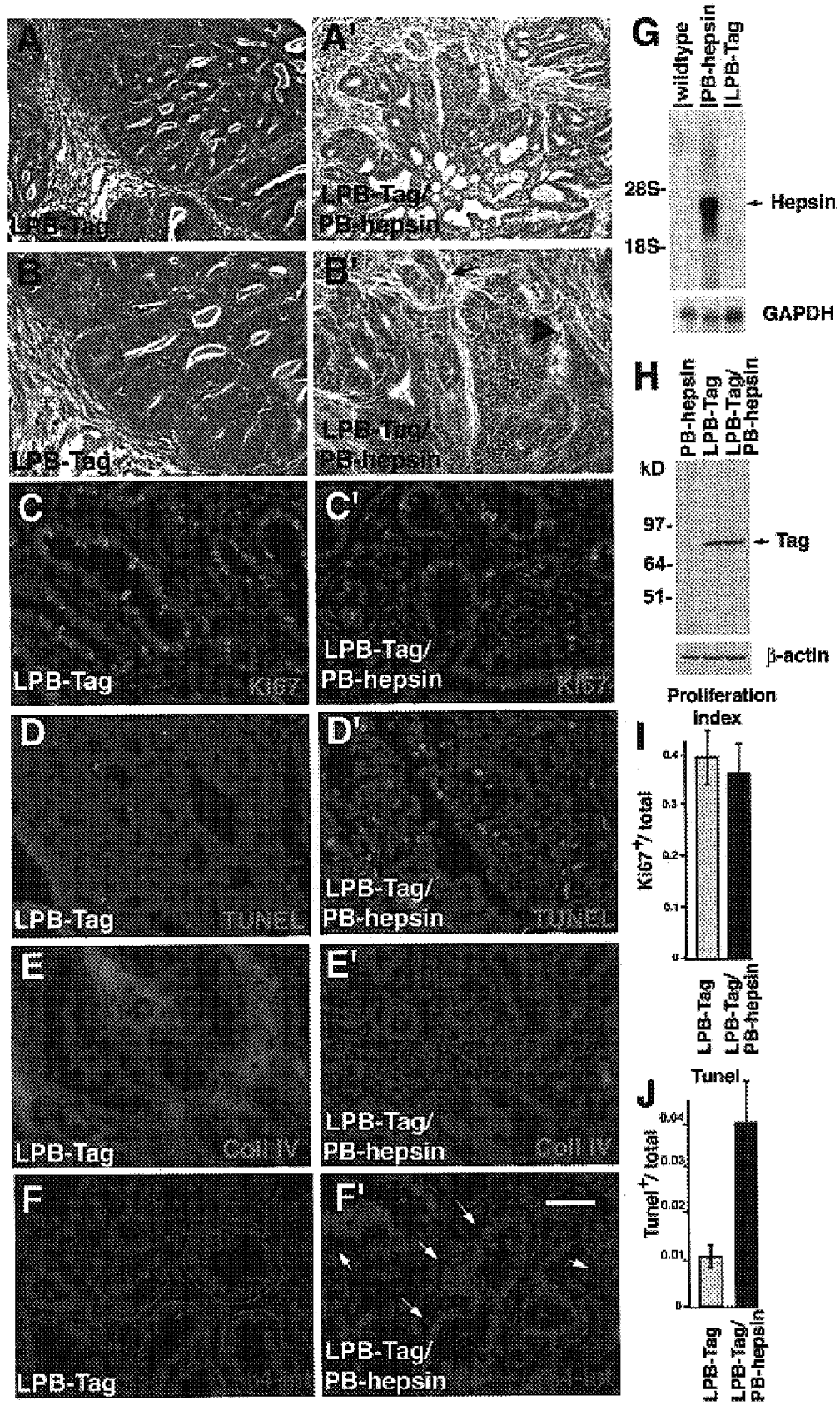
FIG. 5. Hepsin causes disruption of epithelial structure and promotes cancer progression in the SV40 T antigen-driven mouse model of prostate cancer. A-B': Histologic appearance of ventral prostates from 21 week-old LPB-Tag and LPB-Tag/PB-hepsin animals. Note disorganization of epithelial structure, adenocarcinoma with glandular differentiation and foci of poorly differentiated NE adenocarcinoma (arrowhead in B') in LPB-Tag/PB-hepsin animals. C, C': Immunostaining with anti-Ki67 antibodies shows no differences in cell proliferation between LPB-Tag and LPB-Tag/PB-hepsin animals. D, D': Apoptosis is increased in the prostates of LPB-Tag/PB-hepsin mice. Apoptotic cells were detected using TUNEL staining, green. E, E': Decreased staining for Collagen IV in LPB-Tag/PB-hepsin mice, green. F, F': Immunostaining with anti-β4-integrin antibodies (red) reveals disorganization of basement membrane receptors in LPB-Tag/PB-hepsin mice (arrows). G: Endogenous hepsin is not upregulated in the prostate of LPB-Tag mice. RNA was extracted from ventral prostates of wildtype, PB-hepsin, and LPB-Tag animals and analyzed by Northern blot hybridization with hepsin and GAPDH probes. H: Absence of changes in the levels of T-antigen (Tag) in LPB-Tag/PB-hepsin animals. Proteins from ventral prostates of PB-hepsin, LPB-Tag and LPB-tag/PB-hepsin animals were analyzed by Western blotting with anti-Tag and anti-β-actin antibodies. I: Quantitation of the experiments shown in C, C'. Proliferation index determined as a ratio of proliferating cells (Ki67+) to the total cell number. J: Quantitation of experiments shown in D,D'. Number of TUNEL+ cells per total cell numbers were counted. Note that staining with FITC-labeled secondary antibodies was possible because hrGFP fluorescence was too weak to be detected on frozen tissue sections (data not shown). The scale bar in F' represents 66 µm for frames A, A', 33 µm for B-F'.

Staining with Ki67 antibodies revealed no difference in cell proliferation between the prostates of LPB-Tag and LPB-Tag/PB-hepsin animals (FIGS. 5C, C', I, n=3). In contrast, TUNEL staining showed a four fold increase in apoptosis in the double transgenic animals (FIGS. 5D, D', J, n=4).

To determine whether hepsin expression causes changes in the organization of the basement membrane in this model, immunofluorescent staining with antibodies recognizing extracellular matrix proteins was performed. Laminin 5 was absent in both LPB-Tag and LPB-Tag/PB-hepsin prostates. Collagen IV staining was severely reduced in the hepsin-expressing prostates (FIGS. 5E, E', n=2). In addition, β4-integrin staining revealed disorganization and disruption of basement membrane receptors in the LPB-Tag/PB-hepsin double transgenic animals (FIGS. 5F, F', n=3). These changes in staining pattern were similar to changes found in PB-hepsin animals, suggesting hepsin-mediated disorganization of the basement membrane in the LPB-Tag mouse model of prostate cancer. Since cell-substratum adhesion is an important source of cell survival signals, the increase in apoptosis in the LPB-Tag/PB-hepsin animals may be a consequence of the disorganization of the basement membrane, which provides major ligands for cell adhesion receptors.

Hepsin Promotes Prostate Cancer Metastasis

Figure 6:
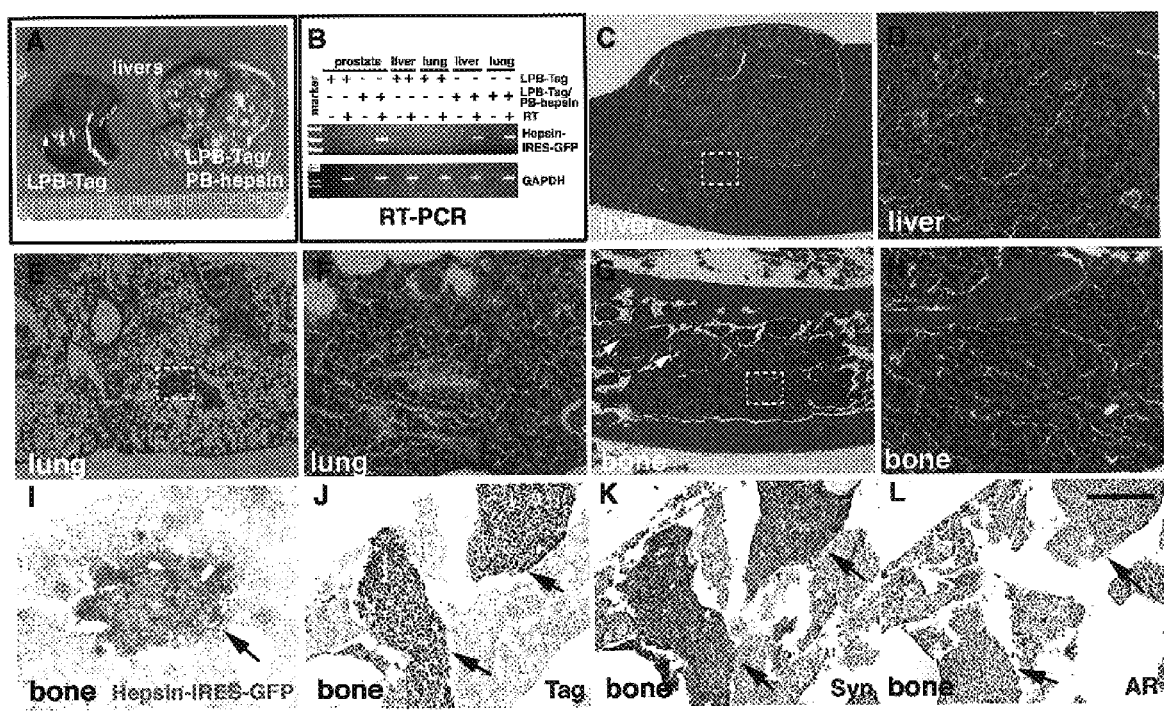
FIG. 6. Hepsin promotes metastasis in the LPB-Tag mouse prostate cancer model. A: Macroscopic appearance of livers from 21 week-old LPB-Tag and LPB-Tag/Hepsin animals. Extensive metastasis was observed in double transgenic mice. B: PB-hepsin transgene expression in prostate metastases to liver and lung from LPB-Tag/PB-hepsin animals. RNA extracted from various organs of LPB-Tag and LPB-Tag/PB-hepsin animals was subjected to RT-PCR analyses with primers specific for PB-hepsin (Hepsin-IRES-GFP) or control GAPDH transcripts. Samples without RT served as controls. C-H: Histologic appearance of liver (C, D), lung (E, F), and bone (G, H) showing prominent metastases in the LPB-Tag/PB-hepsin mice. Areas within dashed squares of C, E, G are shown at higher magnification in D, F, H, respectively. I-L: Bone metastases in LPB-Tag/

Animals from the LPB-Tag 12T-7f line do not display prostate cancer metastases (Kasper et al., 1998). In contrast, by 21 weeks of age up to 65% of double transgenic LPB-Tag/PB-hepsin mice developed prominent metastasis (Table 1, FIG. 6). LPB-Tag/PB-hepsin animals obtained using two independently generated PB-hepsin lines developed metastases, confirming that metastasis was due to hepsin upregulation and not the site of transgene integration. Metastases were observed in the liver, lung and bone of the LPB-Tag/PB-hepsin transgenic animals (Table 2). RNA extracted from the livers and lungs of LPB-Tag/PB-hepsin mice was positive for PB-hepsin transcripts (FIG. 6B). In addition, PB-hepsin mRNA was detectable in the bone metastases by in situ hybridization (FIG. 6I, n=2). These data demonstrate active hepsin expression in the metastatic lesions. Immunohistochemical analysis demonstrated that metastases were also positive for androgen receptor and SV40 large T antigen, confirming their prostatic origin (arrows in FIGS. 6J, L, n=4). Metastatic lesions in other SV40 T antigen-driven mouse models of prostate cancer (TRAMP, CR2-T-Ag, LPB-Tag line 12-T10) display features of NE differentiation (Shappell et al., "Transgenic mouse models of prostate carcinoma: Anatomic, Histopathologic, and molecular considerations," in: *Prostate Cancer: Scientific and Clinical Aspects of Bridging the Gap*, ed. by PD Abel and E-N Lalani, Imperial College Press (London) (2004)). Morphologically, metastases in LPB-Tag/PB-hepsin animals contained tightly packed cells displaying nuclear molding and high nuclear/cytoplasmic ratio that was consistent with features of NE differentiation. Moreover, these metastatic lesions were positive for synaptophysin, a marker of NE cells, confirming their NE differentiation (FIG. 6K, n=4). Overall, upregulation of hepsin in a mouse model of prostate cancer resulted in marked progression of prostatic tumors and caused the development of NE metastatic tumors to the liver, lung and bone.

TABLE 1

| GENOTYPE | TOTAL # OF MICE | # OF MICE WITH METASTASIS |
|---|---|---|
| LPB-TAG | 15 | 0 |
| PB-HEPSIN LINES C AND D | 9 | 0 |
| LPB-TAG/ PB-HEPSIN LINE C | 12 | 5 |
| LPB-TAG/ PB-HEPSIN LINE D | 17 | 11 |

TABLE 2

| Genotype of mice with metastasis | Animal # | Organs displaying metastasis | | | | |
|---|---|---|---|---|---|---|
| | | Liver | Bone | Lung | Kidney | Spleen |
| LPB-Tag/PB-hepsin line C | #41 | + | − | − | − | − |
| | #42 | + | + | + | − | − |
| | #57 | + | − | + | − | − |
| | #77 | + | − | − | − | − |
| | #112 | + | + | + | − | − |
| LPB-Tag/PB hepsin line D | #29 | + | + | − | − | − |
| | #42 | + | + | + | − | − |
| | #43 | + | + | − | − | − |
| | #45 | − | − | + | − | − |
| | #63 | − | − | + | − | − |
| | #71 | + | − | + | − | − |
| | #75 | + | − | − | − | − |
| | #102 | − | + | + | − | − |
| | #133 | − | − | + | − | − |
| | #138 | + | − | − | − | − |
| | #151 | + | − | − | − | − |

Discussion.

The metastatic cascade is a complex process consisting of a number of important steps that include loss of tissue architecture, local invasion, invasion into blood and lymph vessels, extravasation, establishment of the secondary foci and angiogenesis (Robinson et al., *Cancer Treat Res.* 118:1-21 (2004)). Failure to complete any of these steps would result in the absence of metastases. The classic model of the metastatic process assumes that metastases arise from the rare cells that, in addition to the early oncogenic alteration enabling them to form primary tumor, subsequently accumulated novel mutations that promote metastasis.

A recently proposed alternative model suggests that combinations of early oncogenic alterations in the primary tumor determines its metastatic potential (Bernards and Weinberg, *Nature* 418:823 (2002)). This study reveals that hepsin has no impact on cell proliferation and, therefore, it does not act as a classic oncogene. In contrast, increase in hepsin expression leads to disorganization of the basement membrane and promotes primary prostate cancer progression and metastasis. These hepsin functions are consistent with the classic model of metastatic process. On the other hand, the fact that hepsin becomes upregulated very early in the human prostate cancer at the stage of PIN-like lesions is more in line with the alternative model of metastasis. Therefore, it appears that these findings provide some support for both models. It is possible that some middle ground may exist between these seemingly opposing views of metastatic process.

The basement membrane is a specialized extracellular matrix structure which separates the epithelial and stromal cell compartments. Loss of the basement membrane is a mandatory step that occurs during local invasion early in the metastatic process (Abate-Shen and Shen, *Genes Dev.* 14:2410-2434 (2000); Robinson et al., *Cancer Treat Res.* 118:1-21 (2004)). To accomplish local invasion, tumor cells use extracellular and cell-surface proteolytic enzymes to degrade the basement membrane proteins (Chang and Werb, *Trends Cell Biol.* 11:S37-43 (2001); Del Rosso et al., *Clin. Exp. Metastasis* 19:193-207 (2002)). Multiple studies have demonstrated a critical role of matrix metalloproteinases (MMPs) that can degrade the extracellular matrix and basement membrane proteins and facilitate the initial invasion events (Chang and Werb, *Trends Cell Biol.* 11:S37-43 (2001)). Simple inhibition of MMPs, however, is not necessarily beneficial for cancer patients outcome. The roles of MMPs are quite complex, as they have functions other than promotion of metastasis and have substrates other than extracellular matrix proteins (Egeblad and Werb, *Nat. Rev. Cancer* 2:161-174 (2002)). The second, perhaps equally important, group of enzymes involved in degradation of the extracellular matrix and modulation of cell-substratum adhesion is the family of serine proteases (Del Rosso et al., 2002). One of the best-studied serine proteolytic systems at the cell surface is the urokinase-type plasminogen activator (u-PA) and u-PA receptor (u-PAR). The u-PA/u-PAR complex has an intrinsic ability to concurrently regulate pericellular proteolysis and cell surface adhesion receptors.

This study presents the first in vivo evidence that upregulation of type-II cell-surface serine protease hepsin leads to disorganization and disruption of basement membrane. Since hepsin is a serine protease, it is likely that it exercises its function through proteolytic digest of specific substrate proteins. If some of these substrates are the basement membrane proteins, hepsin may be directly involved in degradation of the extracellular matrix. Alternatively, hepsin may activate other proteases that are often synthesized as nonactive proenzymes. By this means it can activate a proteolytic cascade that will ultimately lead to degradation of the extracellular matrix proteins. Experiments with cultured cell lines demonstrated that blood coagulation factor VII may be one of the hepsin proteolytic substrates (Kazama et al., *J. Biol. Chem.* 270:66-72 (1995)). Hepsin can convert factor VII to VIIa and activate the blood coagulation cascade leading to formation of thrombin, deposition of pericellular fibrin and activation of PAR-1. Other type II serine proteases have also been demonstrated to be able to activate proteolytic cascades. MT-SP1, a close relative of hepsin, has been shown to activate PAR-2 and pro-u-PA (Takeuchi et al., *J. Biol. Chem.* 275:26333-26342 (2000)).

Overexpression of hepsin in metastases-derived human prostate cancer cell lines decreases their ability to invade Laminin 1-based matrigel (Srikantan et al., *Cancer Res.* 62:6812-6816 (2002)). This might appear to contradict these findings with in vivo overexpressed hepsin. However, while the in vitro invasion system is capable of deciphering the differences in the matrigel degradation abilities, it cannot assay the initial stages of invasion that include disruption of normal epithelial structure, weakening of cell-substratum adhesion and failure of basement membrane deposition and assembly. The present results demonstrate that hepsin overexpression causes disorganization of the basement membrane and, therefore, is likely to act at the early stages of metastatic pathway.

The type-II serine proteases have been previously implicated in cancer progression (Del Rosso et al., 2002; Netzel-Arnett et al., *Cancer Metastasis Rev.* 22:237-258 (2003); Wu, *Curr. Top Dev. Biol.* 54:167-206 (2003)). The supporting evidence, however, has been mostly circumstantial. Many of these proteins are upregulated in cancer. For example, corin is upregulated in leimyosarcoma, endometrial carcinoma and osteosarcoma (Yan et al., *J. Biol. Chem.* 274:14926-14935 (1999)). The TMPRSS2 and TMPRSS4 are overexpressed in prostate and pancreatic cancers, respectively (Lin et al., *Cancer Res.* 59:4180-4184 (1999); Wallrapp et al., *Cancer Res.* 60:2602-2606 (2000)). Finally, hepsin was found to be overexpressed in prostate and ovarian cancers (Chen et al., 2003; Dhanasekaran et al., 2001; Ernst et al., 2002; Luo et al., 2001; Magee et al., 2001; Stamey et al., 2001; Stephan et al., 2004; Tanimoto et al., *Cancer Res.* 57:2884-2887 (1997); Welsh et al., 2001). Injections of inhibitors of type II serine proteases suppress primary tumor growth and metastasis of human PC3 prostate tumor cells implanted into nude mice (Takeuchi et al., *Proc. Natl. Acad. Sci. USA* 96:11054-11061 (1999)). Tumor cells overexpressing the type II serine protease matriptase show higher incidence of metastasis when they are injected into nude mice (Ihara et al., *J. Biol. Chem.* 277: 16960-16967 (2002)).

The role of hepsin in prostate cancer has been a matter of debate. While all studies agree that hepsin is upregulated in human prostate cancer, it is not clear how hepsin expression levels correlate with patient outcome. While initially it was found that hepsin levels inversely correlate with the recurrence of prostate cancer (Dhanasekaran et al., 2001), a later study revealed a positive correlation (Stephan et al., *J. Urol.* 171:187-191 (2004)). Hepsin overexpression in metastases-derived prostate cancer cell lines decreases their rates of proliferation (Srikantan et al., 2002). Since wild-type mouse prostate epithelial cells do not express endogenous hepsin, it is difficult to estimate how levels of hepsin expression in hepsin-overexpressing transgenic mice compare to hepsin upregulation in human prostate cancer. The level of expression may play an important role in the phenotype. If hepsin is involved in degradation of cell-substratum adhesion proteins and its activity is very high, prostate epithelial cells will not be able to maintain substratum adhesion, will separate from the basement membrane or tissue culture surface and undergo apoptosis. While extracellular matrix degradation is beneficial and sometimes absolutely necessary for initial tumor invasion, it may be less advantageous during the later stages of metastasis formation, where ability to form de novo attachment in distant organs is necessary for metastatic cell survival. It is possible that very high levels of hepsin expression, which are found in a subset of human prostate cancers, may indeed be associated with inhibition of cell growth and better patient survival prognosis. However, moderate levels of upregulation may be sufficient to disrupt the basement membrane and facilitate initial tumor cell spreading, but may not cause complete loss of substratum adhesion and subsequent cell death.

Human prostate cancer metastasizes preferentially to bone. The mechanisms responsible for bone metastasis are not known. Bone metastases are extremely rare in the current mouse models of prostate cancer. Paucity of bone metastases has been one of the major limitations of mouse models of prostate cancer. The present study demonstrates that unlike human prostate epithelial cells, mouse prostate epithelium does not express detectable levels of endogenous hepsin. Exogenous transgene expression of hepsin was sufficient to promote prostate cancer metastasis to the bone, as up to 25% of 21 week-old LPB-Tag/PB-hepsin double transgenic animals exhibited bone metastases. It is important to note that these numbers are likely to be an underestimation since only the femur bones, representing only a small fraction of total bone mass, were analyzed in this study. The bone lesions in the LPB-Tag/PB-hepsin animals do not show obvious osteoblastic or osteolytic characteristics. This is different from human prostate cancer bone metastases that often show osteoblastic characteristics.

Similar to metastatic lesions in other SV40 T antigen-driven mouse models of prostate cancer, metastases in the LPB-Tag/PB-hepsin animals express NE markers. At present, it is not known whether NE markers in these lesions reflect their NE origin, or they emerge during metastatic process as a consequence of epithelial to NE transdifferentiation. Since hepsin promotes prostate cancer progression by disorganization of the basement membrane, and disruption of the basement membrane occurs in both NE and non-NE types of prostate cancer, it is also likely that hepsin will promote metastasis in the mouse models that do not develop NE differentiation markers.

Since hepsin promotes prostate cancer progression and metastasis, specific inhibition of hepsin proteolytic activity may be effective in blocking prostate cancer progression in human patients. Hepsin knockout mice have no phenotype (Wu et al., 1998), suggesting that specific inhibition of hepsin in human patients will not have significant side effects.

In summary, these in vivo studies have revealed a critical role for hepsin in disruption of the basement membrane and promotion of adenocarcinoma and metastasis in a mouse model of prostate cancer. These findings identify hepsin as a metastasis-promoting protein.

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. A transgenic mouse whose genome comprises a hepsin transgene operably linked to a prostate specific promoter, wherein the hepsin transgene is expressed in prostate epithelial tissue, and wherein the transgenic mouse has a disrupted or disorganized prostate basement membrane.

2. The transgenic mouse of claim 1, wherein the hepsin transgene is overexpressed in the prostate epithelial tissue.

3. The transgenic mouse of claim 1, wherein the hepsin transgene is a mouse transgene.

4. The transgenic mouse of claim 1, wherein the hepsin transgene is a cognate, heterologous hepsin transgene.

5. The transgenic mouse of claim 4, wherein the hepsin transgene is a human transgene.

6. The transgenic mouse of claim 1, wherein the prostate specific promoter is a probasin promoter.

7. The transgenic mouse of claim 1, wherein the mouse further expresses a SV40 large T antigen operably associated with a prostate specific promoter.

8. The transgenic mouse of claim 7, wherein the prostate specific promoter is a probasin promoter.

9. The transgenic mouse of claim 7, wherein primary prostate cancer progression or metastasis is increased in the mouse, as compared with a control mouse having the same genetic predisposition, but not expressing the hepsin transgene.

10. The transgenic mouse of claim 9, wherein the transgenic mouse has increased metastasis to the liver, lung or bone.

11. A method of producing a transgenic mouse suitable for screening agents for use in the detection or treatment of prostate cancer, comprising:

forming a plurality of transgenic mice comprising a diploid genome encoding a hepsin transgene operably linked to a prostate specific promoter;

selecting one of the transgenic mice wherein the hepsin transgene is overexpressed to produce a hepsin polypeptide, and wherein the hepsin polypeptide exhibits tissue-specific expression;

breeding the selected transgenic mouse to a mouse of the same species comprising an SV40 T antigen transagene operably linked to a prostate specific promoter integrated in its genome; and selecting one of the progeny transgenic mice overexpressing the hepsin transgene in the prostate wherein said progeny transgenic mice have a predisposition for prostate cancer.

12. The method of claim 11, wherein the hepsin transgene is a mouse transgene.

13. The method of claim 11, wherein the hepsin transgene is a cognate, heterologous transgene.

14. The method of claim 13, wherein the hepsin transgene is a human hepsin transgene.

15. A method of screening an agent for use in the detection or treatment of prostate cancer, comprising:

providing a transgenic mouse comprising a diploid genome, having a genetic predisposition for prostate cancer and encoding a hepsin transgene operably linked to a prostate specific promoter and an SV40 T antigen transgene operably linked to a prostate specific promoter, wherein the hepsin transgene is overexpressed;

contacting the transgenic mouse with the test compound at a dosage of from about 1 ng/kg to about 10 mg/kg; and examining the contacted transgenic mouse to determine whether the test compound affects tumor development, progression or metastasis.

16. The method of claim 15, wherein the dosage of the test compound is from about 10 μg/kg to about 1 mg/kg.

17. The method of claim 15, wherein the test compound does not inhibit hepsin.

18. The method of claim 15, wherein the test compound decreases metastasis to the liver, lung or bone.

19. The method of claim 18, further comprising determining whether the test compound inhibits hepsin.

* * * * *

SEQUENCE LISTING

<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<223> OTHER INFORMATION: PCR primer

<400> SEQUENCE: 1
gcactagtat ggcgaaggag ggtggcc                                    27

<210> SEQ ID NO 2
<211> LENGTH: 27
<212> TYPE: DNA
<213> ORGANISM: Artificial Sequence
<220> FEATURE:
<223> OTHER INFORMATION: PCR Primer

<400> SEQUENCE: 2
gcgaattctc agggctgagt caccatg                                    27

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
aggagatcat gagcttcaag g                                          21

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
gctgtagaac ttgccgctgt                                            20

<210> SEQ ID NO 5
<211> LENGTH: 24
<212> TYPE: DNA
<213> ORGANISM: Artificial Sequence
<220> FEATURE:
<223> OTHER INFORMATION: PCR primer

<400> SEQUENCE: 5
catgtgggcc atgaggtcca ccac                                       24

<210> SEQ ID NO 6
<211> LENGTH: 26
<212> TYPE: DNA
<213> ORGANISM: Artificial Sequence
<220> FEATURE:
<223> OTHER INFORMATION: PCR primer

<400> SEQUENCE: 6
tgaaggtcgg agtcaacgga tttggt                                     26

<210> SEQ ID NO 7
<211> LENGTH: 1296
<212> TYPE: RNA
<213> ORGANISM: mouse

<400> SEQUENCE: 7
gacauggcga aggagggugg ccggacugca gcaugcugcu ccagacccaa gguggcagcu    60
cucauugugg guacccugcu guuccugaca ggcauugggg ccgcguccug gccauugug   120 accauccuac ugcagaguga ccaggagcca cuguaccaag ugcagcucag uccaggggac   180

```
ucacgacuug caguguugga caagacggag gguacgugga ggcuacugug cuccucacgc    240
uccaaugcca ggguggcagg gcucggcugu gaggagaugg gcuuucucag ggcucuggcg    300
cacucggagc uggaugugcg cacucgcggc gccaacggca caucgggcuu cuuuugcgug    360
gacgagggcg gacugccucu ggcucagagg uugcuggaug ucaucucugu augugacugu    420
ccuagaggcc gauccugac ugccaccugc caagacugug gccgcaggaa gcugccggug    480
gaccgcauug uggggggcca ggacagcagu cuggaagu ggccguggca ggucagccug    540
cguuaugaug ggacccaccu cuguggggg ucccugcugu cugggacug ggugcugacu    600 gcugcacauu gcuuccaga gcggaaccgg guccugcuc gguggcgagu auuugcuggu    660
gcuguagccc ggaccucacc ccaugcugug caacggggg uucaggcugu gaucuaucau    720
gggggcuacc uucccuuucg agacccuacu auugacgaaa acagcaauga cauugccuug    780
guccaccucu cuagcucccu gccucucaca gaauacaucc agccagugug ucucccugcu    840
gcgggacagg cccugguggga uggcaagguc uguacuguga ccggcugggg uaacacacag    900
uucuauggcc aacaggcuau ggugcuccaa gaggcccggg uucccaucau aagcaacgaa    960
guuugcaaca gccccgacuu cuacgggaau cagaucaagc caagauguu cugugcuggc   1020 uauccugagg guggcauuga ugcgugccag ggcgacagug gaggcccuu ugugugugaa   1080 gacagcaucu cugggacauc aagguggcgg cuauguggca uuuaagcug gguaccggc    1140 ugugcuuugg cccggaagcc aggaguguac accaaaguca cugacuuccg ggaguggauc   1200
uucaaggcca uaaagacuca cuccgaagcc aguggcaugg ugacucagcc cugauccgcc   1260
cucaucucgc ugcuccgugc ugcacuagca uccaga                             1296
```

<210> SEQ ID NO 8
<211> LENGTH: 416
<212> TYPE: PRT
<213> ORGANISM: mouse

<400> SEQUENCE: 8

```
Met Ala Lys Glu Gly Gly Arg Thr Ala Ala Cys Cys Ser Arg Pro Lys
1               5                   10                  15

Val Ala Ala Leu Ile Val Gly Thr Leu Leu Phe Leu Thr Gly Ile Gly
            20                  25                  30

Ala Ala Ser Trp Ala Ile Val Thr Ile Leu Leu Gln Ser Asp Gln Glu
        35                  40                  45

Pro Leu Tyr Gln Val Gln Leu Ser Pro Gly Asp Ser Arg Leu Ala Val
    50                  55                  60

Leu Asp Lys Thr Glu Gly Thr Trp Arg Leu Leu Cys Ser Ser Arg Ser
65                  70                  75                  80

Asn Ala Arg Val Ala Gly Leu Gly Cys Glu Glu Met Gly Phe Leu Arg
                85                  90                  95

Ala Leu Ala His Ser Glu Leu Asp Val Arg Thr Ala Gly Ala Asn Gly
            100                 105                 110

Thr Ser Gly Phe Phe Cys Val Asp Glu Gly Gly Leu Pro Leu Ala Gln
        115                 120                 125

Arg Leu Leu Asp Val Ile Ser Val Cys Asp Cys Pro Arg Gly Arg Phe
    130                 135                 140

Leu Thr Ala Thr Cys Gln Asp Cys Gly Arg Arg Lys Leu Pro Val Asp
145                 150                 155                 160

Arg Ile Val Gly Gly Gln Asp Ser Ser Leu Gly Arg Trp Pro Trp Gln
                165                 170                 175
```

-continued

```
Val Ser Leu Arg Tyr Asp Gly Thr His Leu Cys Gly Gly Ser Leu Leu
            180                 185                 190
Ser Gly Asp Trp Val Leu Thr Ala Ala His Cys Phe Pro Glu Arg Asn
            195                 200                 205
Arg Val Leu Ser Arg Trp Arg Val Phe Ala Gly Ala Val Ala Arg Thr
        210                 215                 220
Ser Pro His Ala Val Gln Leu Gly Val Gln Ala Val Ile Tyr His Gly
225                 230                 235                 240
Gly Tyr Leu Pro Phe Arg Asp Pro Thr Ile Asp Glu Asn Ser Asn Asp
                245                 250                 255
Ile Ala Leu Val His Leu Ser Ser Ser Leu Pro Leu Thr Glu Tyr Ile
                260                 265                 270
Gln Pro Val Cys Leu Pro Ala Ala Gly Gln Ala Leu Val Asp Gly Lys
            275                 280                 285
Val Cys Thr Val Thr Gly Trp Gly Asn Thr Gln Phe Tyr Gly Gln Gln
        290                 295                 300
Ala Met Val Leu Gln Glu Ala Arg Val Pro Ile Ile Ser Asn Glu Val
305                 310                 315                 320
Cys Asn Ser Pro Asp Phe Tyr Gly Asn Gln Ile Lys Pro Lys Met Phe
                325                 330                 335
Cys Ala Gly Tyr Pro Glu Gly Gly Ile Asp Ala Cys Gln Gly Asp Ser
                340                 345                 350
Gly Gly Pro Phe Val Cys Glu Asp Ser Ile Ser Gly Thr Ser Arg Trp
            355                 360                 365
Arg Leu Cys Gly Ile Val Ser Trp Gly Thr Gly Cys Ala Leu Ala Arg
        370                 375                 380
Lys Pro Gly Val Tyr Thr Lys Val Thr Asp Phe Arg Glu Trp Ile Phe
385                 390                 395                 400
Lys Ala Ile Lys Thr His Ser Glu Ala Ser Gly Met Val Thr Gln Pro
                405                 410                 415
```